United States Patent
Gololobov et al.

(10) Patent No.: US 6,433,078 B1
(45) Date of Patent: Aug. 13, 2002

(54) REVERSIBLY SOLUBLE ENZYME-POLYMER CONJUGATES

(75) Inventors: Mikhail Y. Gololobov, Forest Park, IL (US); Victor M. Ilyashenko, Northborough, MA (US)

(73) Assignee: Polium Technologies, Inc., Shrewsbury, MA (US)

( * ) Notice: Subject to any disclaimer, the term of this patent is extended or adjusted under 35 U.S.C. 154(b) by 0 days.

(21) Appl. No.: 09/694,227

(22) Filed: Oct. 23, 2000

(51) Int. Cl.$^7$ .......................... C08G 63/48; C08G 63/91
(52) U.S. Cl. ...................... 525/54.1; 435/177; 435/178; 435/180; 435/181; 530/812; 530/815; 530/816
(58) Field of Search .......................... 525/54.1; 435/177, 435/178, 180, 181; 530/812, 815, 816

(56) References Cited

U.S. PATENT DOCUMENTS

| | | | |
|---|---|---|---|
| 5,310,786 A | 5/1994 | Vorlop et al. | 525/54.1 |
| 5,739,195 A | 4/1998 | Kroker et al. | 524/459 |

OTHER PUBLICATIONS

Alred, et al., "Application of temperature–induced phase partitioning at ambient temperature for enzyme purification," *Journal of Chromatography A.*, 659:289–298 (1994).
Atassi, et al., "Reaction of Proteins with Citraconic Anhydride," *Methods Enzymol.*, 25:546–553 (1972).
Beltran, et al., "Swelling Equilibria for Weakly Ionizable, Temperature–Sensitive Hydrogels," *Macromolecules*, 24:549–551 (1991).
Chen, et al., "Synthesis of carboxylated poly(NIP A Am) oligomers and their application to form thermo–reversible polymer–enzyme conjugates," *J. Biomater, Sci. Polymer Edn.* 5(4):371–382 (1994).
Chen, et al., "Preparations and properties of temperature–sensitive poly (N–isopropylacrylamide)–chymotrypsin conjugates," *Journal of Molecular Catalysis B:Enyzmatic* 2:233–241 (1997).
Chenault, et al., "Kinetic Resolution of Unnatural and Rarely Occurring Amiono Acids: Enantioselective Hydrolysis of N–Acyl Amino Acids catalyzed by Acylase I," *J. Am. Chem. Soc.*, 111:6354–6364 (1989).
Feder, "A Spectrophotometric Assay for Neutral Protease," *Biochemical and Biophysical Research Cimmunications*, 32(2):326–332 (1968).
Galaev, "'Smart' polymers in biotechnology and medicine," *Russian Chem. Rev.*, 64(5):471–489 (1995).
Galaev, et al., "Affinity Thermoprecipitation Contribution of the Efficiency of Ligand–Protein Interaction and Access of the Ligand," *Biotechnology and Bioengineering*, 41:1101–1103 (1993).
Galaev, et al., "Affinity Thermoprecipitation of Trypsin Using soybean Trypsin Inhibitor Conjugated with a Thermo–Reactive Polymer, Poly(N–Vinyl Caprolactam)," *b. enzyme Microb. Technol.*, Biotechnology Techniques 6(4):353–358 (Mar. 28, 1992).
Habeeb, et al., "Determination of Free Amino Groups in Proteins by Trinitrobenzenesulfonic Acid," *Analytical Biochemistry*, 14:328–336 (1966).
Hayashi, et al., "Protease Immobilization onto Polyacrolein Microspheres," *Biotechnology and Bioengineering* 35:518–524 (1990).
Hoshino, et al., "Preparation of a Novel Thermo–Responsive Polymer and Its Use as a Carrier for Immobilization of Thermolysin," *Journal of Fermentation and Bioengineering*, 83(3):246–252 (1997).
Jaworek, et al., "Enzymes Immobilized by Copolymerization,—Preparation and Properties of Enzymes Immobilized by Copolymerization," *Methods Enzymol.*, 44:195–201 (1976).
Karlstrom, et al., "Phase diagrams of Nonionic Polymer–Water Systems. Experimental and Theoretical Studies of the Effects of Surfactants and Other Cosolutes," *J. Phys. Chem.*, 94:5005–5015 (1990).
Klapper, et al., "Acylation with Dicarboxylic Acid Anhydries," *Methods Enzymol.*, 25:531–536 (1972).
Kubota, et al., Solution Properties of Poly(N–isopropylacrylamide) in Water, *Polymer Journal*, 22(1):15–20 (1990).
Lalonde, et al., "Enzymatic Kinetic Resolution of α–Methyl Carboxylic Acids," *J. Org. Chem.* 53:2323–2327 (1988).
Liu, et al., "Synthesis of thermal Phase Separating Reactive Polymers and Their Applications in Immobilized Enzymes," *Polymer Journal*, 245(6):561–567 (1993).
Meighen, et al., "Hybridization of Native and Chemically Modified Enzymes. II. Native and Succinylated Glyceraldehyde 3–Phosphate Dehydrogenase," *Biochemistry*, 9(5):1177–1184 (1970).

(List continued on next page.)

Primary Examiner—Nathan M. Nutter
(74) Attorney, Agent, or Firm—McAndrews, Held & Malloy, Ltd.

(57) ABSTRACT

The present invention is directed to a method for producing reversibly soluble, catalytically active enzyme-polymer conjugates and the products thereof. In particular, the invention is directed to reversibly soluble catalytically active enzyme-polymer conjugates made by incorporating enzymes modified to contain free vinyl double bonds into reversibly soluble polymers i.e., polymers that reversibly respond to slight changes in the environment, such as temperature, ionic strength, pH, electric fields, etc., during the polymerization reaction. Thus, when modified enzymes are incorporated into reversibly soluble polymers, the biocatalysts obtained can be precipitated without destroying the delicate enzyme(s). Moreover, these biocatalysts can be solubilized again and reused at the initial environmental conditions.

18 Claims, 18 Drawing Sheets

OTHER PUBLICATIONS

Morihara, et al., "α–Chymotrypsin as the Catalyst for Peptide Synthesis," *Biochem. J.*, 163:531–542 (1977).

Nguyen, et al., "Syntheses and Applications of Water–Soluble Reactive Polymers for Purification and Immobilization of Biomolecules," *Biotechnology and Bioengineering*, 34:1186–1190 (1989).

Okahata, et al., "Communications to the Editor," *Macromolecules*, 19:493–494 (1986).

Schild, et al., "Microcalorimetric Detection of Lower Critical solution temperatures in Aqueous Polymer Solutions," *J. Phys. Chem.* 94:4352–4356 (1990).

Shiroya, et al., "Control of enzymatic activity using thermosensitive polymers," *Colloids and Surfaces B: Biointerfaces*, 4:275–285 (1995).

Sun, et al., "Immobilized Chyumotrypsin on Reversibly Precipitable Polymerized Liposome," *Applied Biochemistry and Biotechnology*, 56:331–339 (1996).

Takeuchi, et al., "Temperature–responsive graft copolymers for immobilization of enzymes," *Makromol. Chem.*, 194:1991–1999 (1993).

Wang, et al., "New Carbohydrate–Based Materials for the Stabilization of Proteins," *J. Am. Chem. Soc.*, 114:378–380 (1992).

REVERSIBLY SOLUBLE ENZYME-POLYMER CONJUGATES

This work was funded, in part, by The National Institutes of Health, Grant No. 1R43 GM 60830-01 awarded by the National Institute of General Medical Sciences.

BACKGROUND OF THE INVENTION

Biocatalysts, i.e., free or conjugated enzymes, offer unique advantages over classical chemical methods for producing a wide variety of products. In particular, biocatalysts are highly selective, i.e., able to differentiate between similar molecules or fragments; mild, i.e., minimize side reactions; and are often more environmentally friendly than classical chemical catalysts. However, all biocatalysts on the market either cannot be reused or do not work efficiently in heterogeneous reaction systems. Consequently, biocatalysis, i.e., methods of organic chemistry employing biocatalysts, is often overlooked for large-scale industrial applications.

Biocatalysts are currently commercially available in three forms: free enzymes, immobilized enzymes, and cross-linked enzyme crystal (CLEC®; Altus, Cambridge, Mass.) biocatalysts. Free enzymes are soluble in aqueous reaction systems and act as any other homogeneous catalyst. Free enzymes work well in both homogeneous and heterogeneous reaction systems. However, problems associated with free enzymes include low stability under work-up conditions and significant surface activity of enzyme-containing solutions, especially at high concentrations. This makes the reuse of free enzymes practically impossible and complicates product purification for many large-scale industrial applications. Thus, most free enzymes are not cost-effective for large-scale industrial applications.

Immobilized enzymes are enzymes that are attached to a chemically inert solid carrier. Thus, immobilized enzymes are easier to separate from homogeneous reaction systems than free enzymes. However, most industrial processes involve heterogeneous reaction systems with insoluble starting materials or products or both. On the industrial scale, separating insoluble reaction products from insoluble immobilized enzymes is often the bottleneck in industrial processes and/or not cost-effective. Moreover, the activity of immobilized enzymes in heterogeneous reaction systems constitutes only a fraction of their activity in homogeneous reaction systems [Hayashi, T. & Ikada, Y., *Biotechnol. Bioeng.* 35:518 (1990)]. In addition, the active enzyme content in most commercially-available, covalently bound immobilized enzyme preparations is usually well below 1% by total weight (see Table 1).

TABLE 1

Active protein content of several common, commercially-available immobilized enzyme preparations

| Enzyme | Activity of free enzyme (U/g) | Activity of immobilized enzyme (U/g) | Enzyme content by weight (%) | Source |
|---|---|---|---|---|
| Chirazyme L-2 (Lipase from *Candida antarctica*, type B) | >1,200,000 | 200 3,000 | 0.02 0.25 | Roche, item #s 1836021, 1663917, 1835807 |
| Chirazyme L-3 (Lipase from *Candida rugosa*) | 1,500,000 | 500 | 0.03 | Roche, item #s 1978659, 1965972 |
| Chirazyme L-9 (Lipase from *Mucor miehei*) | 3,000,000 | 10 | 0.0003 | Roche, item #s 1831313, 1827308 |
| b-Chymotrypsin | 40,000–60,000 | 500–1,500 | 1.25–2.5 | Sigma, item #s C 7762, C 5407 |
| Penicillin amidase | 10,000 | 60–120 | 0.6–1.2 | Sigma, item #s P 3319, P 3942 |
| Penicillinase | 1,500,000–3,000,000 | 1,500–4,500 | 0.1–0.3 | Sigma, item #s P 0389, P 8817 |
| Protease from *Staphylococcus aureus* strain 8 | 500,000–1,000,000 | 250–500 | 0.025–0.1 | Sigma, item #s P 2922, P 6552 |

Table 1 provides a comparison of the activities (U/g) of commercially-available free and immobilized enzyme preparations listed in their respective catalogs. The activities shown in Table 1 are corrected for protein content where that information is available in the same catalog for a given preparation. It was assumed that 100% of the protein in a given preparation is active enzyme. Comparisons between the activities of free and immobilized enzymes were made only where activity was measured using the same method. The Roche catalog in some cases gives lower limits of enzyme activity. Therefore, the calculated enzyme content of a particular immobilized enzyme preparation may represent a lower limit of its respective value. However, these data demonstrate that the actual amount of active enzyme in a particular immobilized enzyme preparation is quite low when compared to free enzyme preparations. As a result of the difficulty to reuse immobilized enzymes in heterogeneous reaction systems and the small percentages of active enzyme in commercially-available immobilized enzyme preparations, immobilized enzymes are less preferred than classical chemical techniques for many large-scale industrial applications.

CLEC® biocatalysts are fine enzyme crystals that are cross-linked and, therefore, insoluble in aqueous media. Because CLEC® biocatalysts are insoluble in aqueous media, CLEC® biocatalysts can be more easily separated from soluble starting materials and products than free enzymes. Further, because of their fine structure, CLEC® biocatalyst activity is close to the activity of free enzymes. However, CLEC® biocatalysts are expensive and possess most of the shortcomings of immobilized enzymes. Thus, a need exists for low-cost, reusable industrial enzyme biocatalysts that are able to work in heterogeneous reaction systems with the same activity as free enzymes.

Too fill this void, a few attempts have been made to design reversibly soluble enzyme-biocatalysts. These biocatalysts are reversibly soluble dependent upon minor changes in the reaction environment, such as temperature, salt concentration, pH, etc. Thus, when in the soluble state, reversibly soluble enzyme biocatalysts are able to function effectively in heterogeneous reaction systems. Further, the reversibly soluble nature of these biocatalysts permits precipitation recovery and reuse. Thus, reversibly soluble enzyme biocatalysts overcome the disadvantages of free enzymes, immobilized enzymes and CLEC® biocatalysts with respect to reuse and the ability to function in heterogeneous reaction systems. In all cases, reversibly soluble enzyme biocatalysts are conjugates of an enzyme with a reversibly soluble polymer i.e., reversibly soluble enzyme-polymer conjugates.

Reversibly soluble enzyme-polymer conjugates have been made with the following enzymes: chymotrypsin [Chen, J.-P. & Hsu, M.-S., *J. Molec. Catalysis B: Enzymatic* 2:233 (1997)], trypsin [Shiroya, T., Yasui, M., Fujimoto, K. & Kawaguchi, H., *Colloid Surfaces B: Biointerfaces*, 4:275 (1995)], β-D-glucosidase [Chen, G. & Hoffman, A. S., *J. Biomater. Sci. Polym. Edn.*, 5:371 (1994)], lactate dehydrogenase [Galaev, I. Yu. & Mattiasson, B, *Biotechnol. Bioeng.*, 41:1101 (1993)], thermnolysin [Liu, F., Tao, G. & Zhuo, R., *Polymer J.*, 25:561 (1993)] and lipase [Takeuchi, S., Omodaka, I., Hasegawa, K., Maeda, Y. & Kitano, Y., *Makromol. Chem.*, 194:1991 (1993)]. However, current methods for producing reversibly soluble enzyme-polymer conjugates produce biocatalysts with enzyme activities, on a weight basis, that are usually significantly lower than those of free enzymes.

Significant loss of the enzyme during binding is one of the main shortcomings of current methods for producing enzyme-polymer conjugates. For example, the binding efficiency of a current method for conjugating chymotrypsin to a copolymer of N-iso-propylacrylamide (NIPAAM) and N-acrylosuccinimide is only 30–40% [Chen, J.-P. & Hsu, M.-S., *J. Molec. Catalysis B: Enzymatic*, 2: 233 (1997)]. When conjugating thermolysin to the same copolymer, the binding efficiency is about twice as low as with chymotrypsin [Liu, F., Tao, G. & Zhuo, R., *Polymer J.*, 25: 561 (1993)]. Only 43% of enzyme binds with the polymer in a reaction between thermolysin and a NIPAAM-based copolymer containing oxirane groups [Vorlop, K.-D., Steinke, K., Wullbrandt, D., Schlingmann, M., U.S. Pat. No. 5,310,786 (1994)]. Binding of chymotrypsin to a polymerized liposome gives much better results, i.e., between 36% and 89% of the enzyme was coupled [Suh, Y., Jin, X,-H., Dong, X.-Y., Yu, K. & Zhou, X. Z., *Appl. Biochem. Biotechnol.*, 56: 331 (1996)], but the procedure is quite cumbersome. When enzyme-polymer conjugates were prepared by carbodiimide-assisted coupling of trypsin with carboxylated poly-(NIPAAM), only a small percentage of the total amount of trypsin was bound to the polymer [Chen, G. & Hoffman, A. S., *J. Biomater. Sci. Polym. Edn.*, 5: 371-382 (1994)].

Many enzymes are quite expensive and, from an industrial standpoint, the degree of enzyme incorporation into a polymer is the key parameter affecting cost-effectiveness of the preparation of reversibly soluble enzyme-polymer conjugates. Therefore, current methods for producing reversibly soluble enzyme-polymer conjugates are not cost-effective for large-scale industrial applications. Moreover, while the concept of reversibly soluble enzyme-polymer conjugates catalyzing reactions with insoluble substrates has been demonstrated, there are no examples of their use with insoluble or poorly soluble substrates and/or products of commercial value in which the reversibly soluble enzyme-polymer conjugates could reveal their full potential. No optimization of current methods for producing enzyme-polymer conjugates has been performed. All current methods for producing enzyme-polymer conjugates are hit-and-miss methods and their performance is far from their potential.

SUMMARY OF THE INVENTION

In one aspect, present invention is directed to a method for producing reversibly soluble, catalytically active enzyme-polymer conjugates by incorporating enzymes modified to contain free vinyl double bonds into reversibly soluble polymers ("smart" polymers) during polymerization. Smart polymers precipitate following a slight change in environmental conditions. Thus, when modified enzymes are incorporated into smart polymers, the biocatalysts obtained can be precipitated without destroying the delicate enzyme(s). Later the biocatalyst can be solubilized again at the initial environmental conditions. Therefore, reversibly soluble biocatalysts acquire the advantages of free enzymes (high activity in heterogeneous systems) and those of immobilized enzymes and CLEC® biocatalysts (easy work-up and the possibility of the reuse). In particular, the present method is directed to a process for producing a reversibly soluble, catalytically active enzyme-polymer conjugate comprising:

(a) contacting a free enzyme having at least one free amino group with a modifying agent, the modifying agent having at least one vinyl double bond and an active acylating group, the active group forming an amide bond between the modifying agent and the free amino group of the enzyme and producing a modified enzyme having a free vinyl double bond;

(b) recovering the modified enzyme;

(c) contacting the modified enzyme with a soluble monomer having the structure $R_1R_2CCR_3R_4$, wherein $R_1$ is selected from hydrogen, carboxy or phenyl moieties, $R_2$ is a hydrogen moiety; $R_3$ is selected from hydrogen, methyl, carboxy, sulfo, or 2-pyridine moieties and $R_4$ is selected from hydrogen, methyl, methoxy, aminopropyl, N,N-dimethylaminopropyl, N N-diethylaminopropyl,

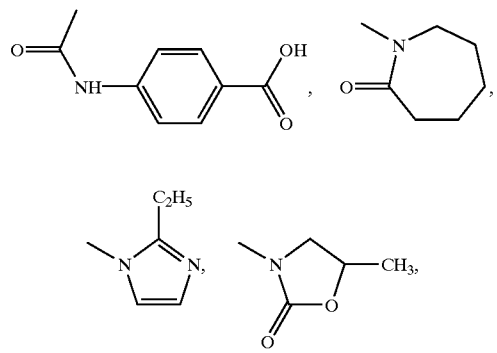

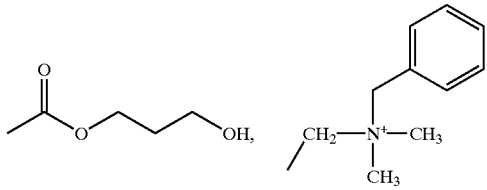

or C(O)NR$_5$R$_6$, wherein R$_5$ is selected from hydrogen, methyl, ethyl, propyl, iso-propyl, or propyl, tetrahydro-pyran-2-yl, 2-methoxy-ethyl, R$_6$ is selected from ethyl, propyl, iso-propyl, cyclo-propyl, tetrahydropyrano-2-yl, 2-methoxy-ethyl, 3-methoxy-propyl, 3-iso-propoxy-propyl or —C(CH$_3$)$_2$—C(O)—NHR$_7$, wherein R$_7$ is selected from methyl, ethyl, iso-propyl, 3-methoxy-propyl or 2,2-diethoxy-ethyl, and wherein the monomer is dissolved in a solution and is selected from a group of monomers which when polymerized contain both hydrophobic and hydrophilic regions; and (d) contacting an initiating agent or agents with the monomer, thereby causing a bond to form between the modified enzyme and the monomer and producing an active enzyme-polymer conjugate that reversibly changes its solubility upon a change in the temperature, salt concentration or pH of the solution.

In another aspect, the invention is directed to a reversibly soluble, catalytically active enzyme-polymer conjugate product.

BRIEF DESCRIPTION OF THE DRAWINGS

FIG. 3 depicts the number of vinyl double bonds introduced into an enzyme by the modification reaction. Specifically.

FIG. 5 depicts the results of visual inspection of the products formed by copolymerization of NIPAAM monomers and chymotrypsin. Specifically.

FIG. 6 depicts the efficiency of the copolymerization reaction of NIPAAM monomers and chymotrypsin modified with either acryloyl chloride (open circles) or itaconic anhydride (closed circles). Specifically.

FIG. 8 depicts the percent enzyme activity of the enzyme-polymer conjugate products of copolymerization of NIPAAM and chymotrypsin modified with either acryloyl chloride (open circles) or itaconic anhydride (closed circles). Specifically.

DETAILED DESCRIPTION OF THE INVENTION

Figure 1:
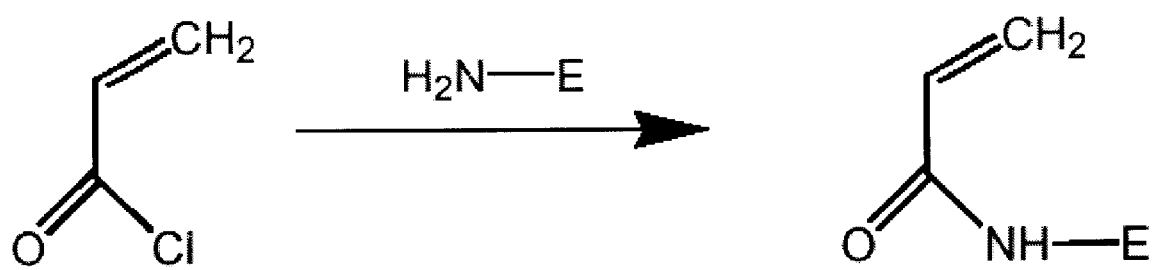
FIG. 1 illustrates the modification reaction of an enzyme (E) with acryloyl chloride.

All successful industrial enzyme-catalyzed processes meet the following requirements: high volumetric productivity; easy work-up; and enzyme reuse. These advantages are also useful for smaller scale processes. Enzyme-catalyzed processes that are able to meet these requirements have two properties in common: (1) the reactions are performed at low enzyme concentrations and (2) the starting materials are very soluble in the reaction media. Low enzyme content means easy work-up. High solubility means higher concentrations of substrate, higher reaction rates and, therefore, higher volumetric productivity. Volumetric productivity is probably the most crucial parameter affecting the economics of industrial processes. Unfortunately, the solubility of most starting materials and products in aqueous media, i.e., media in which enzymes show maximal activity, is limited. Therefore, the reactions have to be performed in heterogeneous systems at high enzyme concentrations, but these conditions make enzyme reuse practically impossible and seriously complicate the work-up.

Accordingly, in one aspect, the present invention is directed to methods for producing low-cost, reusable enzyme biocatalysts that are able to work in heterogeneous reaction systems with the same effectiveness as free enzymes. In particular, the present invention is directed to a method for producing reversibly soluble, catalytically active enzyme-polymer conjugates by incorporating enzymes modified to contain free vinyl double bonds into reversibly soluble polymers ("smart" polymers) during polymerization. In polymer chemistry, the term "smart" is usually applied to systems that reversibly respond to slight changes in the reaction environment, such as temperature, ionic strength, pH, electric fields, etc. The response of smart systems is usually readily visible with the naked eye and consists of the formation of a new phase (a precipitate), sudden swelling or contractions. Thus, when modified enzymes are incorporated into reversibly soluble polymers, the biocatalysts obtained can be precipitated without destroying the delicate enzyme(s). Later the biocatalyst can be solubilized again at the initial environmental conditions. Therefore, reversibly soluble biocatalysts acquire the advantages of free enzymes (high activity in heterogeneous systems) and those of immobilized enzymes and CLEC® biocatalysts (easy work-up and the possibility of reuse).

Specifically, the present method is directed to a process for producing a reversibly soluble, catalytically active enzyme-polymer conjugate comprising:

(a) contacting a free enzyme having at least one free amino group with a modifying agent, the modifying agent having at least one vinyl double bond and an active acylating group, the active group forming an amide bond between the modifying agent and the free amino group of the enzyme and producing a modified enzyme having a free vinyl double bond;

(b) recovering the modified enzyme;

(c) contacting the modified enzyme with a soluble monomer having the structure $R_1R_2CCR_3R_4$, wherein $R_1$ is selected from hydrogen, carboxy or phenyl moieties, $R_2$ is a hydrogen moiety; $R_3$ is selected from hydrogen, methyl, carboxy, sulfo, or 2-pyridine moieties and $R_4$ is selected from hydrogen, methyl, methoxy, aminopropyl, N,N-dimethylaminopropyl, N,N-diethylaminopropyl,

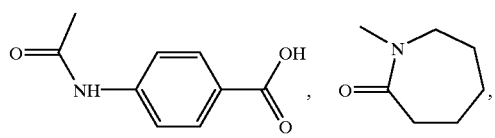

-continued

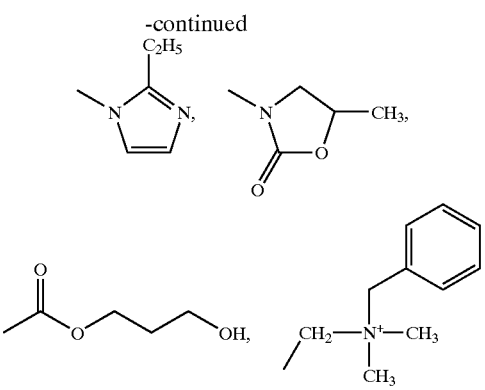

or $C(O)NR_5R_6$, wherein $R_5$ is selected from hydrogen, methyl, ethyl, propyl, iso-propyl, or propyl, tetrahydropyran-2-yl, 2-methoxy-ethyl, $R_6$ is selected from ethyl, propyl, iso-propyl, cyclo-propyl, tetrahydropyrano-2-yl, 2-methoxy-ethyl, 3-methoxy-propyl, 3-isopropoxy-propyl or $-C(CH_3)_2-C(O)-NHR_7$, wherein $R_7$ is selected from methyl, ethyl, iso-propyl, 3-methoxy-propyl or 2,2-diethoxy-ethyl, and wherein the monomer is dissolved in a solution and is selected from a group of monomers which when polymerized contain both hydrophobic and hydrophilic regions; and (d) contacting an initiating agent or agents with the monomer, thereby causing a bond to form between the modified enzyme and the monomer and producing an active enzyme-polymer conjugate that reversibly changes its solubility upon a change in the temperature, salt concentration or pH of the solution.

In another aspect, the invention is directed to a reversibly soluble catalytically active enzyme-polymer conjugate product.

Unlike other biocatalysts, reversibly soluble, catalytically active enzyme-polymer conjugates can be used advantageously in heterogeneous reactions. The most obvious example is a heterogeneous reaction system consisting of a suspension of starting materials and products. In this case, the reversibly soluble enzyme-polymer conjugate is introduced into the suspension of starting materials. The enzyme-polymer conjugate dissolves and acts as any other soluble enzyme. After conversion of the starting materials to precipitated product, the product can be easily separated by a filtration. The enzyme-polymer conjugate remains in the reaction mixture. A slight change in the temperature, salt concentration or pH in the reaction environment causes the enzyme-polymer conjugate to precipitate. The biocatalyst can then be filtered and reused. After the reaction, the reaction mixture usually contains contaminants that make biocatalyst isolation before the next cycle mandatory. If native enzymes were used instead of reversibly soluble enzyme-polymer conjugates, precipitation of free enzymes would require the use of reagents and conditions that would inevitably denature the free enzymes.

Other heterogeneous reaction systems are biphasic, i.e., systems consisting of an aqueous phase, in which the enzyme biocatalyst is dissolved, and a water-immiscible organic solvent phase containing most of the starting materials and the products. These reactions have to be performed under vigorous stirring, and the formation of stable emulsions is a common problem in biphasic systems. Such emulsions are stabilized by enzymes that are natural surface-active compounds. Therefore, the enzyme content in biphasic systems has to be kept to a minimum. Otherwise, stable emulsions formed at high enzyme content make large scale work-up economically impractical. However, this requirement limits the choice of starting materials because the reaction rates for most enzyme-catalyzed reactions are low at low enzyme concentrations. Reversibly soluble enzyme-polymer conjugates overcome this limitation. A reversibly soluble, catalytically active enzyme-polymer conjugate dissolves in the aqueous phase of a biphasic solvent system. Thus, the reversibly soluble nature of catalytically active enzyme-polymer conjugates avoids the formation of an emulsion. After the desired reaction is finished, the reversibly soluble, catalytically active enzyme-polymer conjugates can be precipitated and filtered, the phase layers can be easily separated and any target compound dissolved in the organic phase can be easily recovered. In biphasic systems, the advantage of reversibly soluble, catalytically active enzyme-polymer conjugates over other biocatalysts lies in both enzyme reuse and simplified work-up.

The following theory is offered as a possible way the invention works. The scope of the present invention is not limited by the accuracy or applicability of this theory. Monomers preferred for use in the present method produce polymers that contain both hydrophilic and hydrophobic regions, which allow these polymers to precipitate from the reactant solution with changes in temperature and/or salt concentration. This macromolecular transition occurs abruptly at what is known as the lower critical solution temperature (LCST). The exact LCST of a given polymer is a function of its microstructure and salt concentration. The precipitation occurs because higher temperature and/or higher ionic strength reduce the number of water molecules around hydrophobic regions of the polymer forcing the polymer to precipitate. Thermodynamically, this behavior can be explained by changes in free energy ($\Delta G$) that consist of two terms, enthalpy and entropy: $\Delta G = \Delta H - T\Delta S$ (where $\Delta H$ denotes the enthalpy, T denotes temperature and $\Delta S$ denotes the entropy changes). Spontaneous processes are accompanied by a decrease in free energy. Dissolution of a solute having both hydrophobic and hydrophilic regions in water requires the reorientation of water molecules around the hydrophobic regions of the solute because water molecules are unable to form hydrogen bonds with these regions. This results in negative entropy and, therefore, a positive—$T\Delta S$ term. When the temperature increases, the entropy term starts dominating the exothermic term because of the formation of hydrogen bonds between hydrophilic (polar) polymer regions and the water molecules that were the initial driving force during dissolution. Thus, the free energy becomes positive and the only way to make it negative again is to precipitate the polymer, i.e., to replace the polymer-water contacts with the polymer-polymer and water-water contacts because this results in an increase in entropy.

The driving force behind the polymer salting-out is somewhat different. As the water molecules arrange themselves around salt ions in the solution, the entropy of the system decreases and the—$T\Delta S$ term increases. The free energy becomes positive and precipitation is the only way to make it negative again. Temperature and salt concentration complement each other. Actually, salt just decreases LCST.

Polymers with a wide variety of LCST have been synthesized [Galaev, I. Yu. & Mattiasson, B., *Enzyme Microb. Technol.*, 15: 354–366, (1993); Okahata, Y., Noguchi, H, & Seki, T., *Macromolecules*, 19:493 (1986)]. However, delicate enzyme structure imposes serious limitations on which polymers are suitable for use in the current method. Enzymes are usually quite stable at high salt concentration and at any temperature between 0° C. and 40° C. However, enzymes are usually less stable at temperatures above 40° C. Therefore, an LCST below 40° C. is the main requirement imposed on monomers that are to be used in the present invention for producing thermoresponsive enzyme-polymer conjugates.

Monomers that may be used in the present method have the generic chemical formula (Generic Formula I):

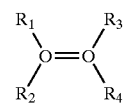

Individual species of monomers having Generic Formula I are represented in Table 2.

TABLE 2

Individual species of monomers having Generic Formula I

| Ligand Species | $R_1$ | $R_2$ | $R_3$ | $R_4$ |
|---|---|---|---|---|
| 1 | hydrogen | hydrogen | carboxy | methyl |
| 2 | hydrogen | hydrogen | carboxy | hydrogen |
| 3 | carboxy | hydrogen | carboxy | hydrogen |
| 4 | phenyl | hydrogen | sulfo | hydrogen |
| 5 | hydrogen | hydrogen | carboxy | aminopropyl |
| 6 | hydrogen | hydrogen | 2-pyridine | hydrogen |
| 7 | hydrogen | hydrogen | carboxy | N'N-dimethylaminopropyl |
| 8 | hydrogen | hydrogen | carboxy | N'N-diethylaminopropyl |
| 9 | hydrogen | hydrogen | hydrogen | methoxy |

There is also a group of monomers suitable for use in the present method comprising Generic Formula I in which $R_1$, $R_2$ and $R_3$ are hydrogens and $R_4$ belongs to a group of substituents wherein the resulting monomer has to be considered a derivative of the $R_4$ group and not a derivative of ethene. These monomers are listed below under their full chemical names:

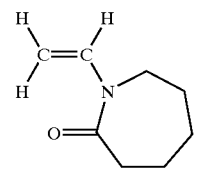

1-Vinyl-azepan-2-one
(N-vinyl-caprolactam)

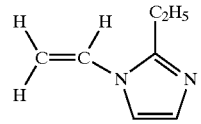

2-Ethyl-1-1H-imidazole

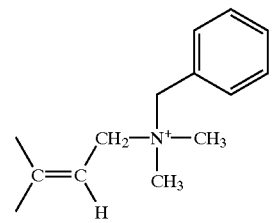

Vinylbenzyldimethylammonium

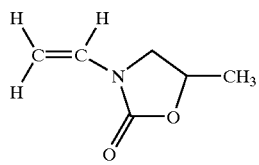

5-Methyl-3-vinyl-oxazolidin-2-one

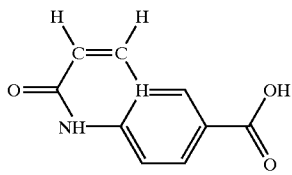

N-acryloyl-p-aminobenzoic acid

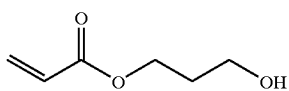

Carboxyethene 3-hydroxy-propyl ester

Finally, there is another group of more preferred monomers for producing reversibly soluble, catalytically active enzyme-polymer conjugates which are N-substituted acrylamides, and include N-iso-propylacrylamide (NIPAAM). Formally they can be depicted by the same general formula $R_1R_2C=CR_3R_4$, where $R_1$, $R_2$ and $R_3$ are hydrogens and $R_4$ is a substituted carboxylic acid amide moiety: —$C(O)NR_5R_6$, which is illustrated by the generic chemical formula (Generic Formula II):

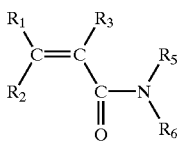

Individual species of monomers having Generic Formula II are represented in Table 3.

TABLE 3

Individual species of monomers having Generic Formula II

| Ligand Species | $R_3$ | $R_5$ | $R_6$ |
|---|---|---|---|
| 1 | hydrogen | hydrogen | ethyl |
| 2 | hydrogen | hydrogen | propyl |
| 3 | hydrogen | hydrogen | iso-propyl |
| 4 | hydrogen | hydrogen | cyclo-propyl |
| 5 | hydrogen | hydrogen | tetrahydro-pyran-2-yl |
| 6 | hydrogen | hydrogen | 3-methoxy-propyl |
| 7 | hydrogen | hydrogen | 3-iso-propoxy-propyl |
| 8 | hydrogen | methyl | 2-methoxy-ethyl |
| 9 | hydrogen | methyl | iso-propyl |
| 10 | hydrogen | ethyl | ethyl |
| 11 | hydrogen | iso-propyl | 2-methoxy-ethyl |
| 12 | hydrogen | propyl | 2-methoxy-ethyl |
| 13 | hydrogen | ethyl | 2-methoxy-ethyl |
| 14 | hydrogen | 2-methoxy-ethyl | 2-methoxy-ethyl |
| 15 | methyl | hydrogen | 3-iso-propoxy-propyl |

TABLE 3-continued

Individual species of monomers having Generic Formula II

| Ligand Species | $R_3$ | $R_5$ | $R_6$ |
|---|---|---|---|
| 16 | hydrogen | hydrogen | —C(CH3)2—CO—NH—$R_7$ |
| 17 | | | where |
| 18 | | | $R_7$ = methyl |
| 19 | | | ethyl |
| 20 | | | iso-propyl |
| 21 | | | 3-methoxy-propyl |
| 22 | | | 2,2-diethoxy-ethyl |

Suitable monomers for the synthesis of reversibly soluble, catalytically active enzyme-polymer conjugates include the following monomers N-iso-propylacrylamide [Kubota, K., Fujishige, S. & Ando, I., *Polym. J.* 22:15 (1990), Hoshino, K., Taniguchi, M., Kawaberi, H., Takeda, Y., Morohashi, S. & Sasakura, T., *J. Ferment. Bioeng.* 83:46 (1997)] and other N-alkylacrylamides [Beltran, S., Baker, J. P., Hooper, H. H., Blanch, H. W. & Prausnitz, J. M., *Macromolecules* 24:529 (1991)]; methyl vinyl ester [Schild, H. G. & Tirrell, D. A., *J. Phys. Chem.*, 94:4352 (1990); N-vinylcaprolactam (NVCL) [Galaev, I. Yu. & Mattiasson, B., *Enzyme Microb. Technol.*, 15:354 (1993)]; ethylene oxide—propylene oxide copolymers [Alred, P. A., Kozlowski, A., Harris, J. M. & Tjernerd, F., *J. Chromatogr.*, A 659:289 (1994)]; polymerized liposomes [Suh, Y., Jin, X.-H., Dong, X.-Y., Yu, K. & Zhou, X. Z., *Appl. Biochem. Biotechnol.*, 56:331 (1996)]; and some cellulose derivatives [Karlstrom, G., Carlsson, A. & Lindmann, B., *J. Phys. Chem.*, 94:5005 (1990)]. Preferred monomers for use in the current method are NIPAAM and NVCL with NIPAAM being the most preferred monomer.

The direct coupling of an enzyme to poly-(NIPAAM) is impossible because poly-(NIPAAM) is an inert polymer. However, several strategies have been used to overcome this problem. The first strategy was to synthesize a copolymer of N-iso-propylacrylamide with a monomer containing reactive groups, e.g., the COOH-groups of acrylic acid [Chen, J.-P. & Hsu, M.-S., *J. Molec. Catalysis B: Enzymatic*, 2: 233 (1997)] or oxirane groups [Nguyen, A. L. & Luong, J. H. T., *Biotechnol. Bioeng.*, 34: 1186 (1989), Vorlop, K.-D., Steinke, K., Wullbrandt, D., Schlingmann, M., U.S. Pat. No. 5,310,786 (1994)]. However, enzyme coupling to the polymer was often inefficient because it involves the interaction of two large macromolecules. This results in both poor binding efficiency of enzyme to polymer and low activities of enzyme-polymer conjugate products. The second strategy was to synthesize terminally modified oligomers of NIPAAM propylacrylamide and then couple them to a protein via a modified terminal group [Chen, G. & Hoffmnan, A. S., *J. Biomater. Sci. Polym. Edn.*, 5: 371 (1994)]. However, the synthesis of terminally-modified oligomers is tedious and labor consuming.

Due to steric hindrance, the present method might not be suitable for producing reversibly soluble, catalytically active enzyme-polymer conjugates with enzymes that have a large molecular weight or with multimeric enzymes having two or more subunits. However, the present method is suitable for producing enzyme-polymer conjugates with a wide variety of enzymes that would be advantageous in large-scale industrial applications, as well as smaller scale applications. As the examples below show, the current method is suitable for producing reversibly soluble, catalytically active enzyme-polymer conjugates with the following enzymes: chymotrypsin, subtilisin and PS lipase. However, one of ordinary skill in the art will appreciate the applicability of the present method for producing reversibly soluble, catalytically active enzyme-polymer conjugates with a wide variety of enzymes.

Suitable modifying agents for use in the present method include acryloyl chloride and itaconic anhydride. Acryloyl chloride has already been used for the introduction of vinyl double bonds into chymotrypsin [Jaworek, D., Botsch, H., Maier, J., *Methods Enzymol.*, 44:195 (1976)]. However, in addition to its lachrymatory properties, acryloyl chloride is not soluble in aqueous media and has to be introduced into the modification reaction in ether. The effectiveness of the reaction depends on the stirring rate, reaction vessel configuration, blade shape and other parameters that affect mass transfer. These parameters are difficult to control during scale-up for industrial reactions. The use of cyclic anhydrides for amino-group protection and protein modification has also been published in the prior art. However, in contrast to itaconic anhydride, prior art examples, i.e., citraconic anhydride [Atassi, M. Z. & Habeeb, A. F. S. A., *Methods Enzymol.*, 25:546 (1972)], maleic anhydride, [Jaworek, D., Botsch, H., Maier, J., *Methods Enzymol.*, 44:195 (1976)], and succinic anhydride [Klapper, M. H. & Klotz, M., *Methods Enzymol.*, 25:531 (1972), Meighen, E. A. & Schachman, H. K., *Biochemistry*, 9:1177 (1970)], do not contain vinyl double bonds or do not form stable amide bonds. To the best of the inventor's knowledge, neither acryloyl chloride or itaconic anhydride has been used for the preparation of reversibly soluble, catalytically active enzyme-polymer conjugates.

As shown herein, reversibly soluble, catalytically active enzyme-polymer conjugates were made using N-isopropylacrylamide (NIPAAM) and N-vinylcaprolactam (NVCL). NIPAAM was chosen for three reasons: (1) NIPAAM is commercially available and very inexpensive; (2) the reversibly soluble properties of poly-(NIPAAM) have been studied extensively [see Galaev, I. Yu., *Russian Chem. Rev.*, 64:471 (1995)]; and (3) NIPAAM shows reversibly soluble properties starting from a molecular mass of 2–3 kDa with an LCST almost independent of molecular mass [Kubota, K., Fujishige, S. & Ando, I., *Polym. J.*, 22:15 (1990)]. The lower the molecular weight of the attached polymer, the higher the expected weight activity of the final product. NVCL was chosen because this monomer and poly-NVCL are extremely non-toxic and biocompatible compounds. Enzymes used included chymotrypsin, subtilisin Carlsberg and PS lipase. Two modifying agents were also tested: acryloyl chloride and itaconic anhydride.

The following are illustrative examples and are not intended to limit the present method to the examples provided as one of ordinary skill in the art could appreciate the applicability of the present method to other compositions and materials.

Abbreviations

Benzyloxycarbonyl, Cbz; acetyl, Ac; ethyl, Et; benzoyl, Bz; p-nitroanilide, pNa; benzoyl-L-tyrosine p-nitroanilide, BzTyrpNA; dimethyl formamide, DMF; dimethyl sulfoxide, DMSO; N-iso-propylacrylamide, NIPAAM; N,N,N',N',-tetramethylethylenediamine, TEMED; N-vinylcaprolactam, NVCL; 2,4,6-trinitrobenzensulfonic acid, TNBS. All amino acid residues were of the L-configuration.

Materials and Equipment

NIPAAM, TEMED, NVCL, itaconic anhydride, acryloyl chloride, solvents and salts were purchased from Aldrich Chemical Company (St. Louis, Mo.). CbzPhe, AcPheOEt, LeuNH$_2$ HCl, TNBS, chymotrypsin (α-form), glucose and the Lowry micro method kit were purchased from Sigma Chemical Company (St. Louis, Mo.). Chymotrypsin (E.C. 3.4.21.1) used in the present method was of highest available purity (Sigma catalog number C 4129; 3× crystallized from 4× crystallized chymotrypsinogen; dialyzed, salt-free lyophilized powder). It was assumed that this preparation contains 100% pure active protein. PS lipase used in the present method was a gift from Amano USA. Subtilisin Carlsberg (E.C. 3.4. 21.62) used in the present method was purchased from Sigma as a crystallized and lyophilized powder. According to our measurements, the protein content by weight of the PS lipase (Amano) and subtilisin Carlsberg (Sigma) was 30% and 50% by weight, respectively. In both cases, it was assumed that all of the protein present in these preparations was active. Spectrophotometric measurements were performed using the Beckman DU 520 UV/VIS spectrophotometer. A VirTis freeze-drier was used to lyophilize the samples.

EXAMPLE 1

Protein Assays

The protein concentration of native enzyme and modified enzyme was determined by measuring absorbance at 280 nm ($E_{280}^{1\%}$=20.4). The protein concentration of enzyme-polymer conjugates was determined using the Lowry micro method.

EXAMPLE 2

Enzyme Assays

The activity of native and conjugated chymotrypsin was determined by measuring BzTyrpNA hydrolysis. A stock solution of 10 mM BzTyrpNA was prepared in DMF. The reaction was performed in 40 mM Tris buffer (pH 8.0) containing 5 mM of CaCl$_2$ with 0.25 mM BzTyrpNA at 25° C. The rate of the BzTyrpNA hydrolysis was measured by monitoring the change of absorbance at 405 nm ($\epsilon_{405}$=9600 M$^{-1}$ cm$^{-1}$). The activity of subtilisin Carlsberg was determined using the same method but different substrate: Cbz-Gly-Gly-L-LeupNA. The rate of hydrolysis was measured by monitoring Cbz-Gly-Gly-L-LeupNA hydrolysis at 400 nm ($\epsilon_{400}$=8000 M$^{-1}$ cm$^{-1}$). The activity of PS lipase was determined in a 50 mM phosphate buffer, pH 7.5, using p-nitrophenyl propionate ($\epsilon_{400}$=8000 M$^{-1}$ cm$^{-1}$). The stock substrate solution (10 mM) was prepared in DMF; the substrate concentration in the cuvette was 0.5 mM.

EXAMPLE 3

Enzyme Modification

For modification with acryloyl chloride (see FIG. 1), enzyme (100 mg) was dissolved in 1 M triethanolamine buffer (pH 8.0) containing 2 mM EDTA and chilled to about 5° C. Acryloyl chloride solution in cold ether was added slowly to the enzyme-TEA solution with constant stirring. The volume of acryloyl chloride solution added to the enzyme is preferably in the range of about 0.5 ml to about 2.5 ml of acryloyl chloride per gram of enzyme; more preferably about 1.5 ml of acryloyl chloride per gram of enzyme. The resultant solution was stirred for an additional 30 minutes. The aqueous phase was removed and dialyzed overnight against distilled water using dialysis tubing with a molecular weight cutoff of 10–14 kDa.

Figure 2:
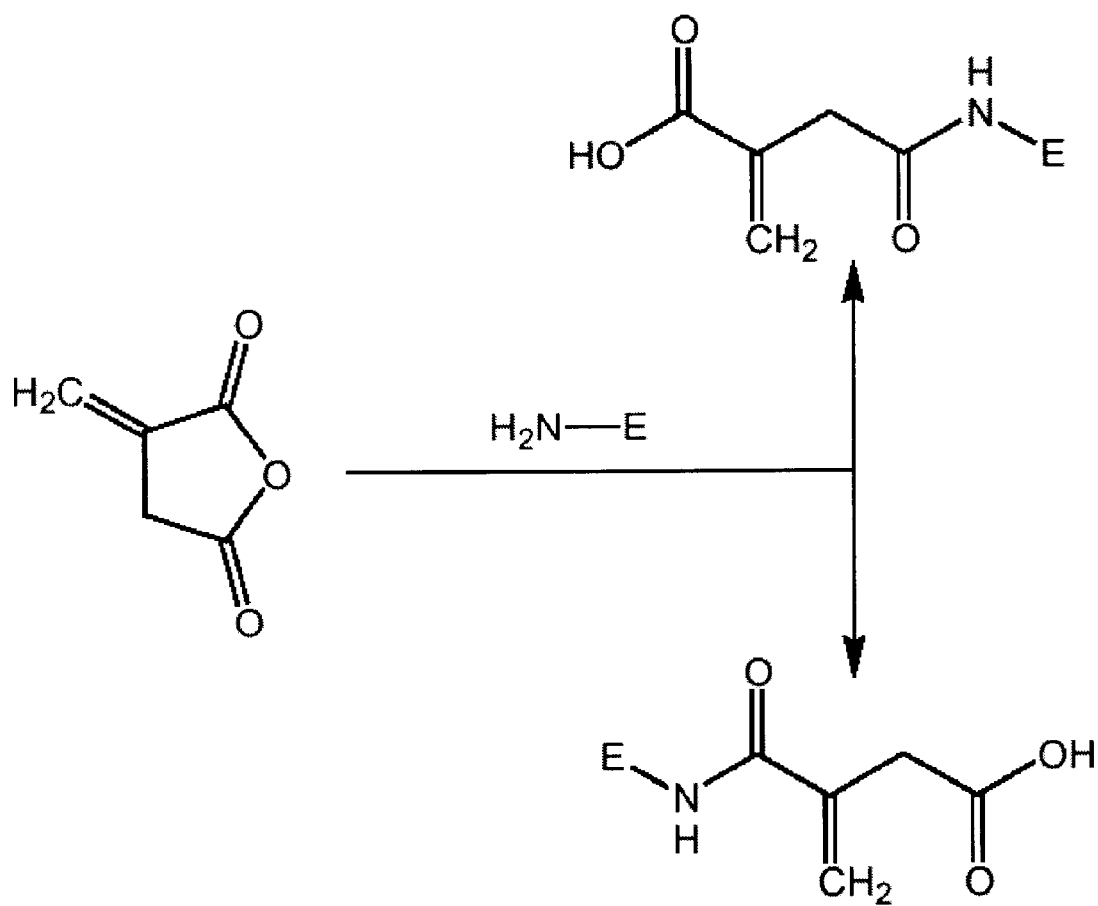
FIG. 2 illustrates the modification reaction of an enzyme (E) with itaconic anhydride.

For modification with itaconic anhydride (see FIG. 2), enzyme (10 mg) was dissolved in 10 ml 0.1 M phosphate buffer (pH 7.8) with constant stirring. In one set of reactions, the phosphate buffer solution contained 5% glucose. Varying amounts of itaconic anhydride were added slowly, while maintaining pH between 7 and 8 with the addition of 1 N NaOH with constant stirring. The amount of itaconic anhydride added to the enzyme is preferably in the range of about 0.2 mg–to about 2 mg of itaconic anhydride per mg of enzyme; more preferably about 1 mg to about 1.5 mg of itaconic anhydride per mg of enzyme. The resultant solution was stirred for an additional 30 minutes, while maintaining the pH between 7 and 8. Then the solution was dialyzed overnight against distilled water using dialysis tubing bags with a molecular weight cutoff of 10–14 kDa.

EXAMPLE 4
Determination of the Average Number of Vinyl Double Bonds Introduced by Enzyme Modification The average number of vinyl double bonds introduced into the modified enzyme during enzyme modification was determined by measuring the average number of the amino groups in the enzyme before and after modification. Quantitative determination of the amino groups in the native and modified enzyme was performed with a TNBS assay [Habeeb, A. F. S. A., *Anal. Biochem.*, 14: 328 (1966)]. Serial dilutions of native and modified enzyme were treated with a TNBS solution under identical conditions.

The results of these experiments, were expressed as $A=\epsilon[E]n$, where A is the absorbance, $\epsilon$ is the molar extinction coefficient of the product formed when TNBS reacts with an amino group of a compound, n is the average number of the amino groups in the whole population of enzyme molecules. Before modification: $A_{nat}=\epsilon[E]n_{nat}$; after modification: $A_{mod}=\epsilon[E]n_{mod}$. Subscripts "nat" and "mod" refer to native and modified enzyme, respectively. Therefore, $n_{mod}=Rn_{nat}$, where R is the slope of the absorbance—enzyme concentration dependence for the modified enzyme divided by the slope of the absorbance—enzyme concentration dependence for the native enzyme. The average number of vinyl double bonds equals introduced by enzyme modification equals $n_{nat}-n_{mod}$ or $n_{nat}(1-R)$. The fact that protein content was maximal at a certain average number of vinyl double bonds per molecule does not mean that all enzyme molecules have this particular number of vinyl double bonds. The TNBS assay does not test vinyl double bond distribution for a mixture of enzyme molecules.

Figure 3A:
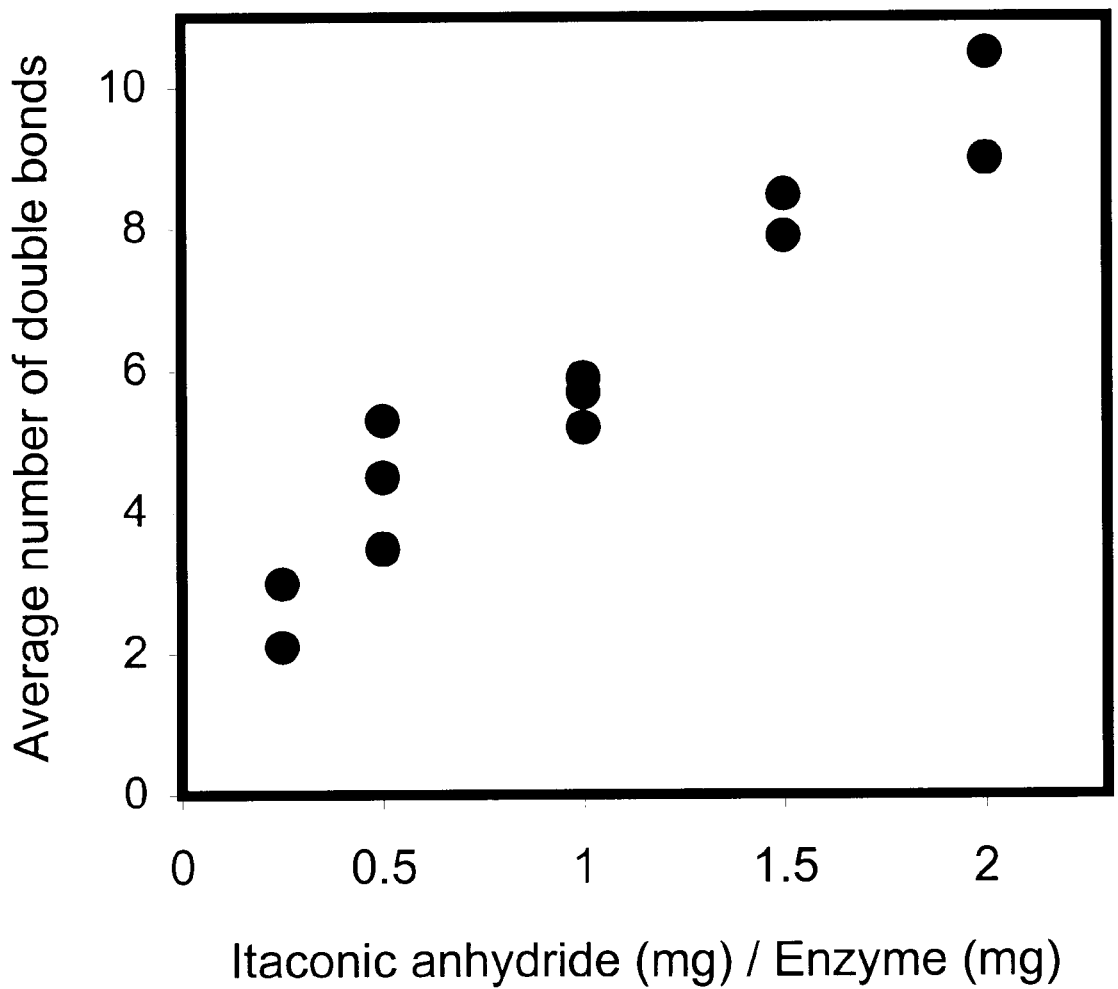
FIG. 3A depicts the number of vinyl double bonds introduced into chymotrypsin by modification with itaconic anhydride as a function of the ratio of itaconic anhydride to chymotrypsin (mg/mg).

The results for modified chymotrypsin are shown in FIG. 3. There are 14 amino groups available in native chymotrypsin. As shown in FIG. 3A, the average number of vinyl double bonds introduced into chymotrypsin by modification with itaconic anhydride produced a maximum of about 10 modified amino groups per molecule, which is very near the theoretical limit for the 14 amino groups of chymotrypsin. The number of vinyl double bonds introduced with itaconic anhydride is very reproducible. Further, there is a linear dependence between the average number of introduced vinyl double bonds and the amount of itaconic anhydride used during enzyme modification.

Figure 3B:
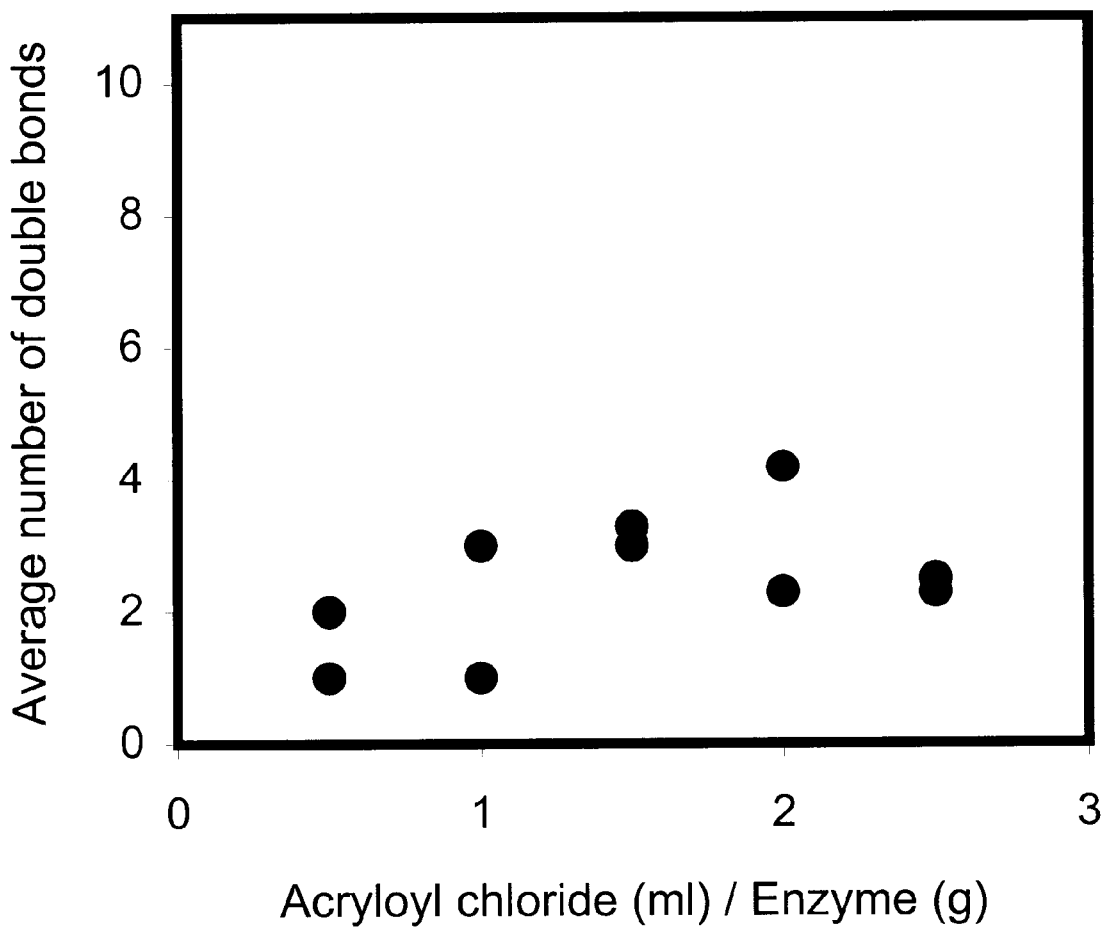
FIG. 3B depicts the number of vinyl double bonds introduced into chymotrypsin by modification with acryloyl chloride as a function of the ratio of acryloyl chloride to chymotrypsin (ml/g).

As shown in FIG. 3B, for enzyme modified with acryloyl chloride, the number of vinyl double bonds introduced by enzyme modification with acryloyl chloride did not appear to be dependent on the amount of acryloyl chloride used. The degree of vinyl double bond incorporation and reproducibility were lower for enzyme modification with acryloyl chloride than for enzyme modification with itaconic anhydride. Most probably, this is because of the biphasic nature of the reaction with acryloyl chloride. Generally, modification with itaconic anhydride is easier to handle and leads to a higher average number of vinyl double bonds in the modified enzyme than modification with acryloyl chloride.

EXAMPLE 5
Enzyme Activity Following Enzyme Modification

Figure 4:
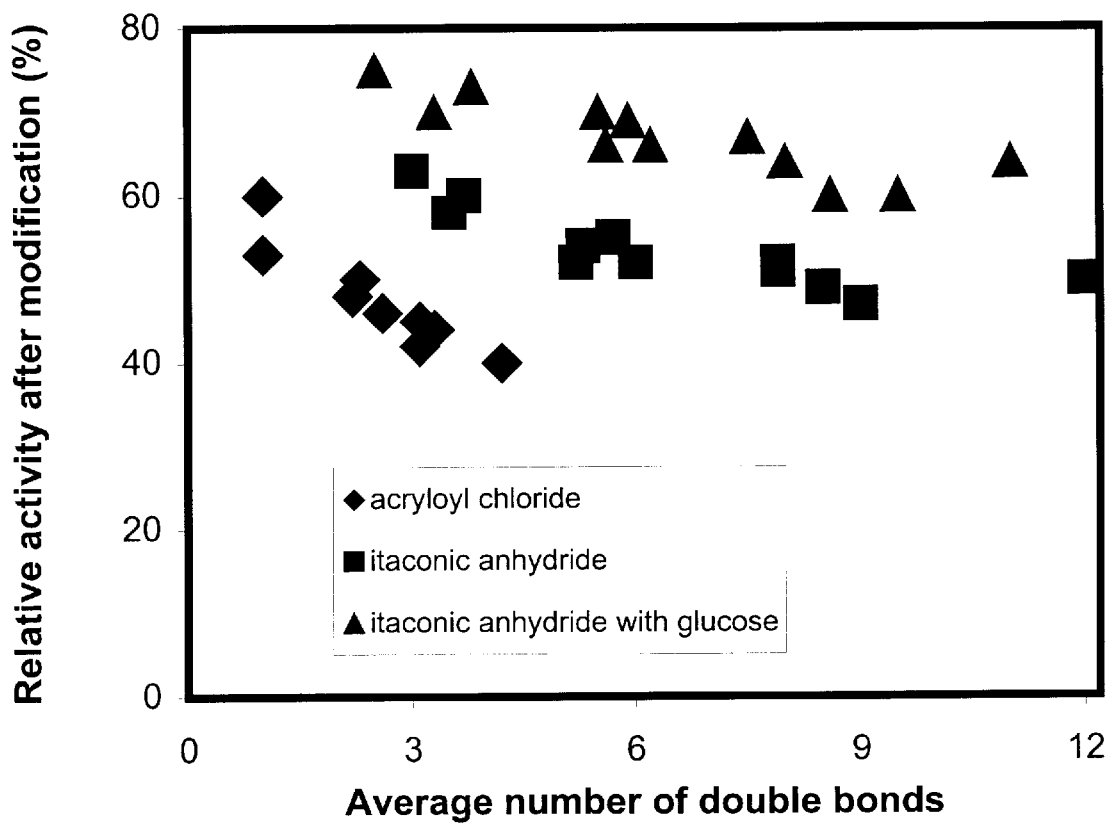
FIG. 4 depicts the relative percent of chymotrypsin activity after modification with either acryloyl chloride (closed diamond), itaconic anhydride (closed squares) and itaconic anhydride with glucose (closed triangles) compared to the average number of double bonds introduced into chymotrypsin by the modification reaction; where relative percent activity after modification equals the product of the total enzyme units after modification divided by the total enzyme units before modification multiplied by 100.
Figure 5A:
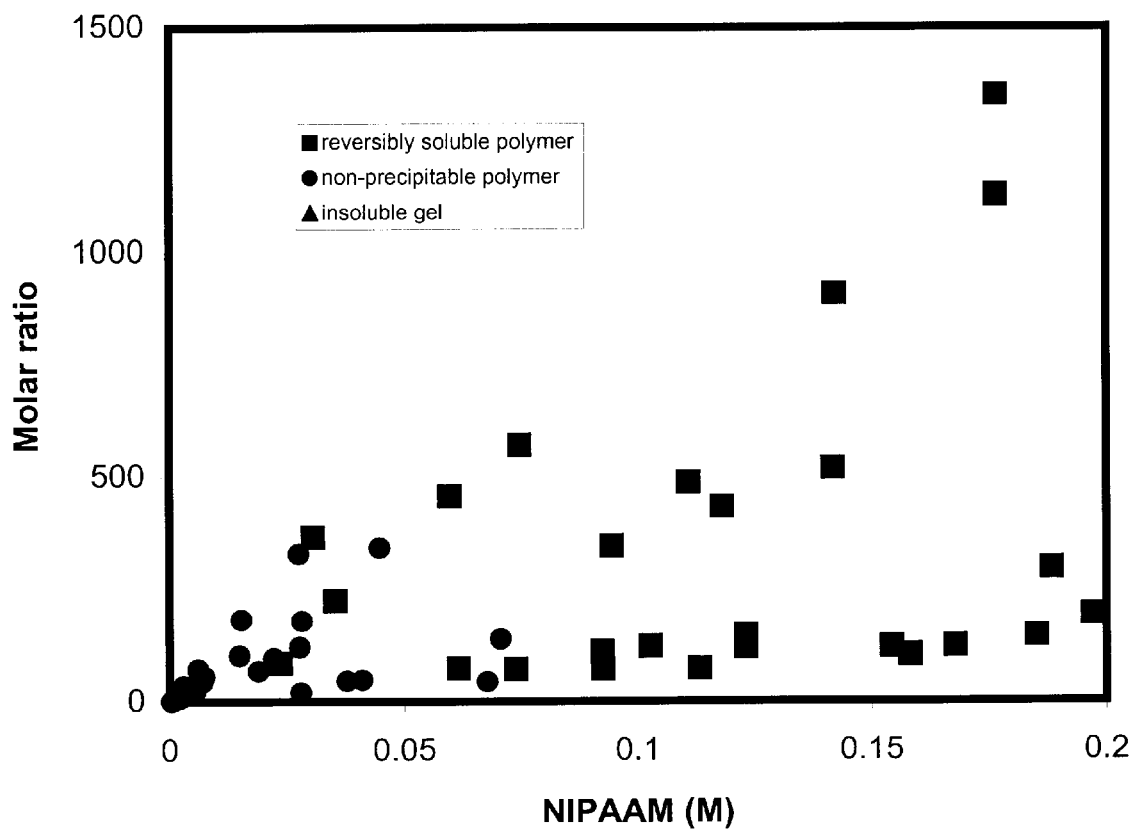
FIGS. 5A and 5B depict the results of visual inspection of the products formed by copolymerization of NIPAAM monomers and chymotrypsin modified with itaconic anhydride at two different ranges of NIPAAM concentration.
Figure 5B:
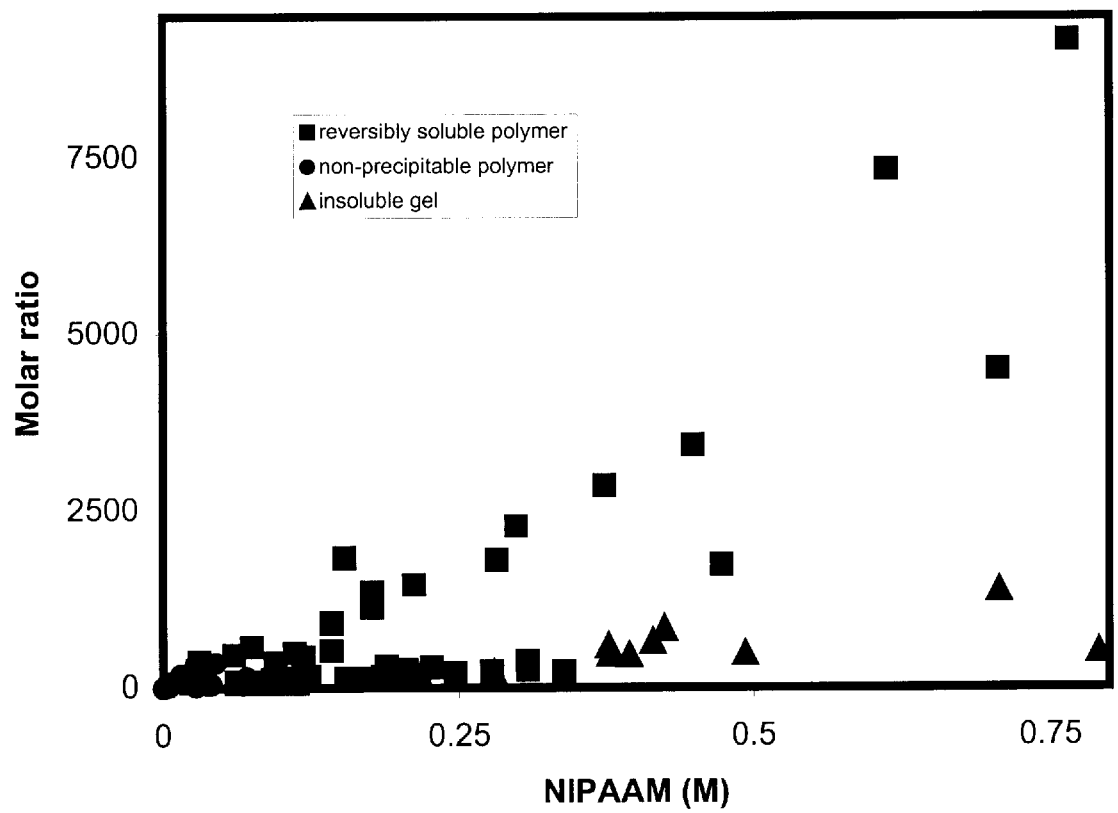
Figure 5C:
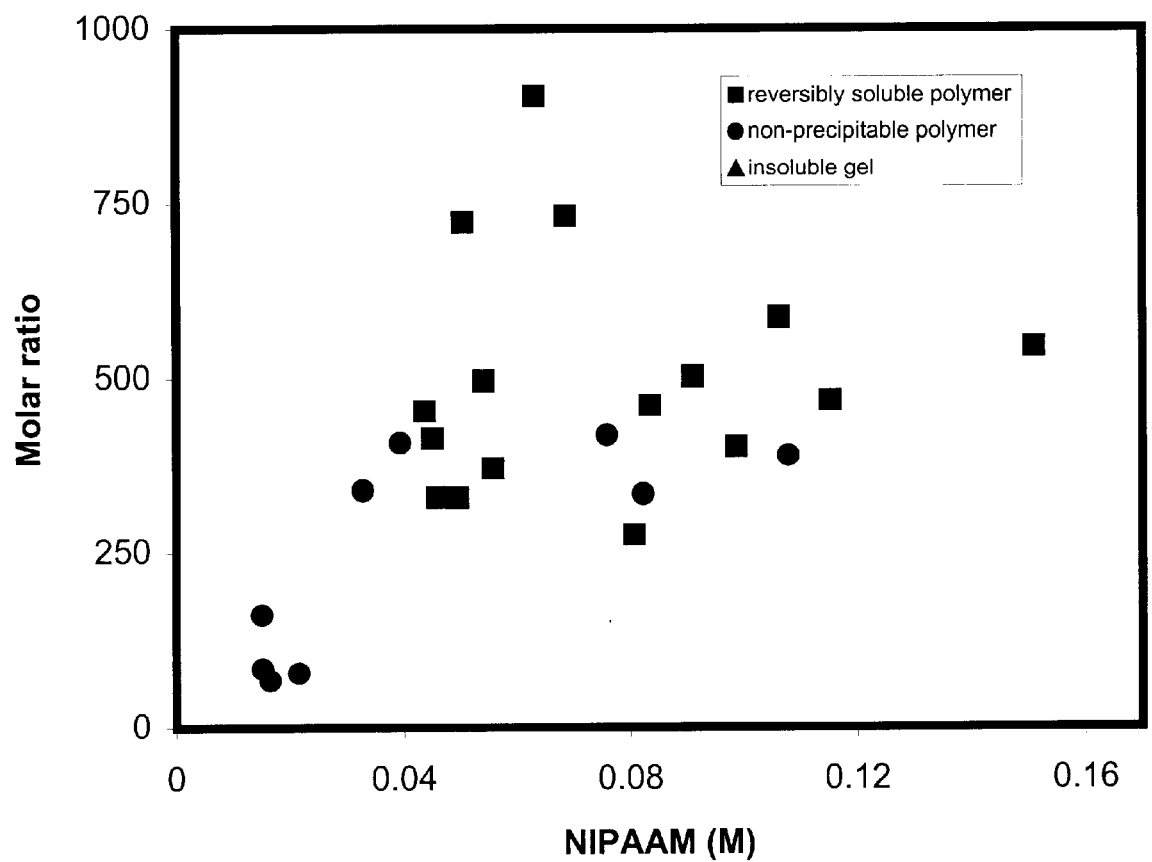
FIGS. 5C and 5D depict the results of visual inspection of the products formed by copolymerization of NIPAAM monomers and chymotrypsin modified with acryloyl chloride at two different ranges of NIPAAM concentration; where a reversibly soluble product is indicated by a closed square, a non-precipitatable product is indicated by a closed circle, and an insoluble gel product is indicated by a closed triangle; and where molar ratio is equal to [NIPAAM]/([E] multiplied by the number of double bonds).
Figure 5D:
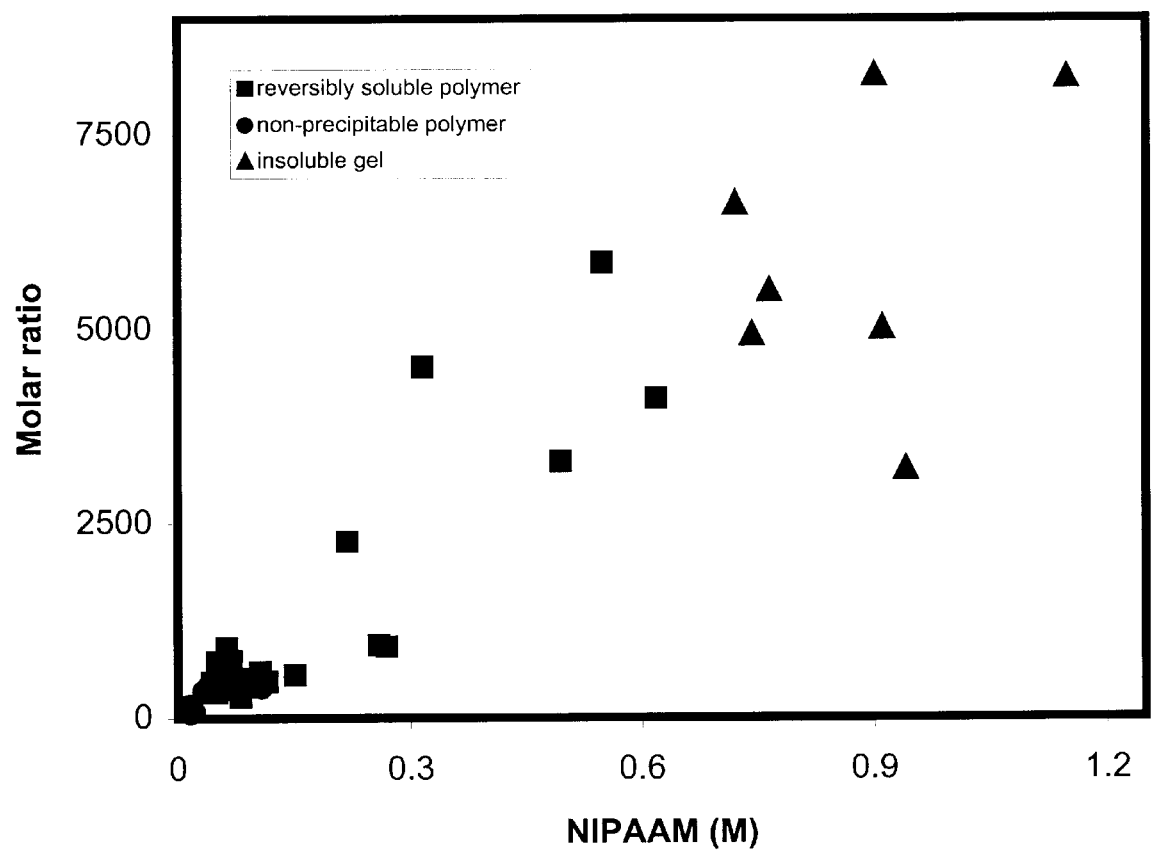

FIG. 4 shows the percentage of chymotrypsin activity remaining after modification with itaconic anhydride and acryloyl chloride. While both methods of modification produced some loss of enzyme activity, the residual activity is generally quite high: up to 75% of non-modified enzyme. The activity loss was generally higher after modification with acryloyl chloride than after modification with itaconic anhydride. For modification with itaconic anhydride, the residual activity was between 47% and 75% of the native enzyme. For modification with acryloyl chloride, the residual activity was between 40% and 60% of the native enzyme. The addition of 5% glucose significantly increased residual activity. While the mechanism of glucose stabilization is has not been determined [Wang, P., Hill, T. G., Wartchow, C. A., Huston, M. E., Oehler, L. M., Smith, M. B., Bednarski, M. D. & Callstrom, R., *J. Am. Chem. Soc.*, 114: 378 (1992)], sugars are often used in commercial enzyme preparations for stabilization purposes. The remaining activity decreased with the number of introduced vinyl double bonds, but this effect was not pronounced.

EXAMPLE 6
Polymerization of Modified Enzyme with NIPAAM

NIPAAM-based reversibly soluble enzyme biocatalysts were prepared with modified chymotrypsin, modified subtilisin Carlsberg and PS lipase. 0.05–130 mg of NIPAAM was added on a per ml basis to a solution of modified enzyme in 10 mM phosphate buffer, pH 7.0– 7.5 and then the resultant solution was carefully degassed. Polymerization was initiated by the addition of 10% $(NH_4)_2S_2O_8$ (1 µl per mg of NIPAAM) and TEMED (0.1 µl per mg of NIPAAM). Other suitable initiating agents include: $Na_2S_2O_6$, 2,2'-azobis(2-aminopropane)dihydrochloride and 2,2'-azobis[2-(2-imidazoline-2-yl)propane]dihydrochloride. Copolymerization of the modified enzyme with NIPAAM did not necessarily result in a reversibly soluble enzyme-polymer conjugate. If the polymer chain is too short, the product will stay in solution at any temperature. On the other hand, at high NIPAAM concentrations, the nascent polymer can attach simultaneously to more than one molecule of the modified enzyme, thereby, causing the formation of a stable, insoluble gel due to cross-linking. For these reasons, after 3 hours, some samples formed insoluble gels and were removed. Transparent samples were diluted with an equal volume of 5 M NaCl, warmed to 37–40° C. and the residue (if any) was filtered. The precipitate was dissolved in cold distilled water and precipitated again as described above. Up to four precipitation—dissolution cycles were performed. After the last cycle, the solution was lyophilized in cold water.

The likelihood of gel formation increases with increases in both the number of vinyl double bonds in the modified enzyme and NIPAAM concentration. To establish the range of both NIPAAM concentration and enzyme concentration at which gel formation is likely, copolymerization was performed at different NIPAAM concentrations with modified enzyme samples containing different numbers of vinyl double bonds. The samples were visually inspected at room temperature and after heating to 40° C. Gel samples were insoluble at any temperature. Reversibly soluble samples were soluble at room temperature and precipitated at 40° C. Non-precipitatable copolymer was soluble at any temperature.

The results for NIPAAM-chymotrypsin enzyme-polymer conjugates are shown in FIG. 5. These data show that NIPAAM concentrations between 0.05 M and 0.6 M and a molar ratio of NIPAAM to enzyme between 350 and 5000 are suitable for producing reversibly soluble enzyme-polymer conjugates. It is important that the NIPAAM/enzyme ratio be divided by the average number of vinyl double bonds in the modified enzyme. When itaconic anhydride was used as a modifying agent, the average number of introduced vinyl double bonds is 2–10 fold higher than when acryloyl chloride is used. Therefore, the same molar ratios correspond to significantly higher enzyme concentrations and lower NIPAAM concentrations for enzyme-polymer conjugates prepared by modification with acryloyl chloride when compared to the enzyme-polymer conjugates prepared with itaconic anhydride. The data in FIG. 5 do not address the enzyme activity of the enzyme-polymer conjugates. However, the data indicate: that, preferably, 40 mg of NIPAAM is added on a per ml basis to a 5 mg/ml solution of modified enzyme.

As expected, non-precipitatable, low molecular weight enzyme-polymer conjugates formed at low concentrations of NIPAAM. Under the same conditions without enzyme, NIPAAM at these concentrations forms reversibly-soluble polymers. Because pure NIPAAM always formed reversibly soluble enzyme-polymer conjugates at these concentrations, the lower degree of polymerization in the presence of enzyme was probably the result of a lower reactivity of the vinyl double bonds in the modified enzyme compared to NIPAAM. Further, the enzyme may act as a radical scavenger.

In contrast, the likelihood of producing an insoluble gel increases with increased NIPAAM concentration. For enzymes modified with itaconic anhydride, this likelihood is higher for a small molar ratio of NIPAAM to enzyme. A small molar ratio indicates either high enzyme content or a large number of introduced vinyl double bonds. If an enzyme molecule contains too many vinyl double bonds, copolymerization of enzyme with NIPAAM may decrease due to steric hindrance. For enzyme modified with acryloyl chloride, the likelihood of producing an insoluble gel is higher at higher NIPAAM concentrations, but also at a higher molar ratio of NIPAAM to enzyme. This is most probably because the range of variation in the average number of double bonds introduced by enzyme modification with acryloyl chloride was much narrower than the range of variation in the average number of double bonds introduced by enzyme modification with itaconic anhydride, thereby, making NIPAAM concentration the main parameter influencing gel formation. Unfortunately, this hypothesis cannot be tested because the TNBS assay only provides information about the average number of vinyl double bonds introduced into a mixture of enzyme molecules and does not provide information about distribution. However, this information is unnecessary because these data show that a molar ratio of NIPAAM to enzyme between 350 and 5000 is suitable for producing a reversibly soluble enzyme-polymer conjugates by the present method.

Figure 6A:
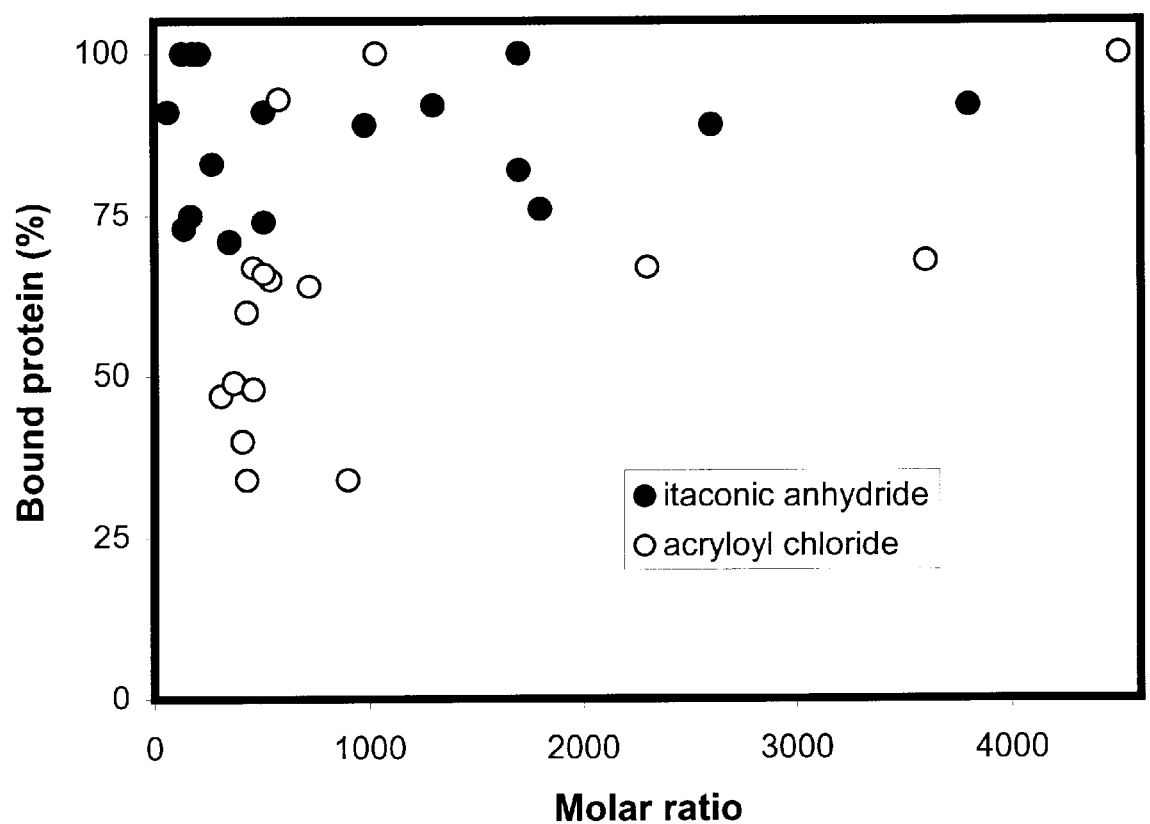
FIG. 6A depicts the efficiency of the copolymerization reaction of NIPAAM monomers and chymotrypsin as a function of the percent bound protein and molar ratio.
Figure 6B:
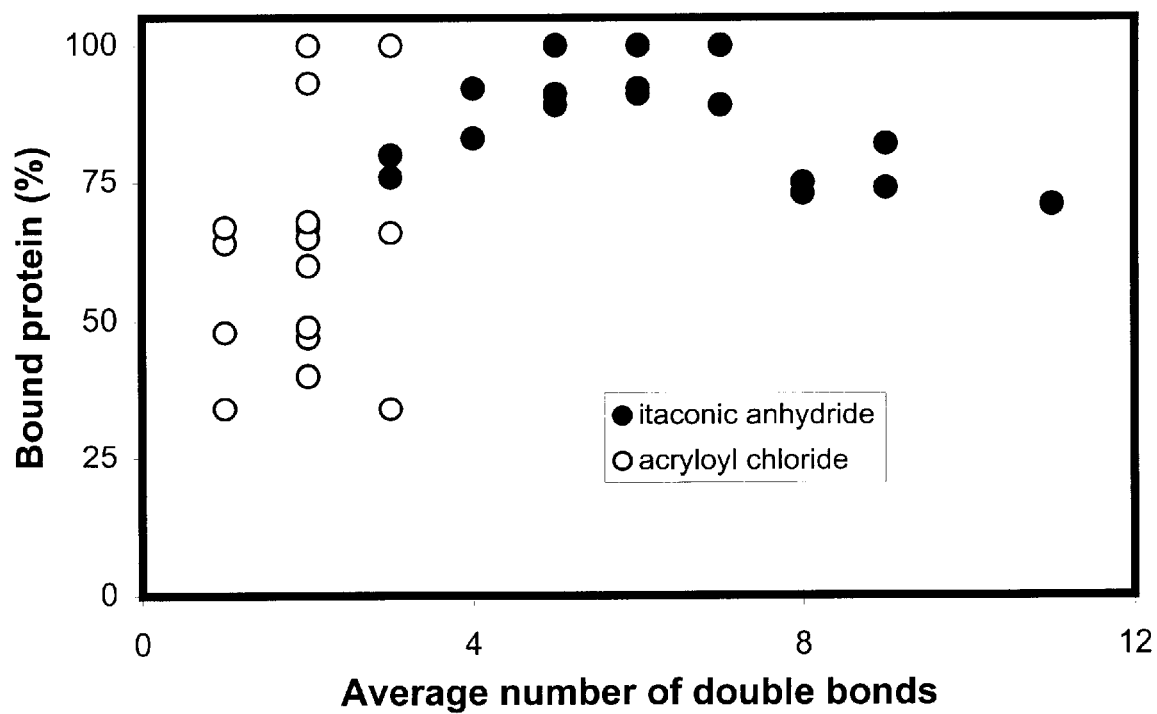
FIG. 6B depicts the efficiency of the copolymerization reaction of NIPAAM monomers and chymotrypsin as a function of the percent bound protein and the average number of double bonds introduced by modification; where the percent bound protein equals the ratio of bound protein (by weight) to the total protein used (by weight) multiplied by 100; and where molar ratio equals ([NIPAAM]/([E]×(the number of double bonds)).

FIG. 6 shows these data alternatively expressed as the percent bound protein, i.e., protein content in enzyme-polymer conjugates, where:

$$\text{Bound protein (\%)} = \frac{\text{Bound protein (by weight)}}{\text{Total protein used (by weight)}} 100\%$$

$$\text{Molar ratio} = \frac{[\text{NIPAAM}]}{[\text{Enzyme}](\text{number of double bonds})}$$

The fact that the amount of enzyme incorporated into the conjugate was maximal at a particular average number of vinyl double bonds per enzyme molecule does not mean that all of the enzyme molecules in a particular experiment had this particular number of double bonds. Also, it does not mean that all of the double bonds introduced into an enzyme molecule participate in the copolymerization reaction. For conjugation, the copolymerization of just one bond is enough. It may be that the enzyme content in the conjugate increases with an increase in the average number of double bonds simply because the likelihood of copolymerization with at least one double bond is higher when more double bonds are available to participate in the copolymerization reaction. However, if an enzyme molecule contains too many vinyl double bonds, the number of enzyme molecules incorporated into the conjugate may decrease due to steric hindrance. Poorer reproducibility of the results for enzyme modified with acryloyl chloride may be the result of a wider double bond distribution for this modifying agent.

However, for both modification agents, the effectiveness of incorporation significantly exceeded the best literature results. For example, Chen et al. reported binding efficiencies of only 30–40% for binding chymotrypsin to "pre-polymerized" copolymer of NIPAAM and N-acrylosuccinimide [Chen, J.-P. & Hsu, M.-S., *J. Molec. Catalysis B: Enzymatic*, 2:233 (1997)]. The binding efficiency of thermolysin to the same polymer is about twice as low [Liu, F., Tao, G. & Zhuo, R., *Polym. J.*, 25:561 (1993)]. Similarly, a binding efficiency of only 43% has been reported for a reaction between thermolysin and a NIPAAM-based copolymer containing oxirane groups [Vorlop, K.-D., Steinke, K., Wullbrandt, D. & Schlingmann, M., U.S. Pat. No. 5,310,786 (1994)]. When reversibly soluble biocatalysts are prepared by the carbodiimide-assisted coupling of trypsin with carboxylated poly-(NIPAAM), only a small percentage of the total amount of trypsin binds to the polymer [Chen, G. & Hoffman, A. S., *J. Biomater. Sci. Polym. Edn.* 5:371 (1994)]. Binding of chymotrypsin to a polymerized liposome gives better results, (between 36% and 89%) [Suh, Y., Jin, X-H., Dong, X.-Y., Yu, K. & Zhou, X. Z., *Appl. Biochem. Biotechnol.*, 56:331 (1996)], but this technology is not suitable for large-scale industrial applications.

In contrast, the present methods yield products in which practically all of the modified enzyme is incorporated into the final product. This is certainly the result of the differences between the published methods and the methods of the present invention. In all published methods, enzymes were conjugated to "pre-polymerized" polymers. In the present method, the polymer grows around the modified enzyme, achieving almost 100% incorporation of the modified enzyme into the enzyme-polymer conjugate in several experiments, and at least about 50% in most experiments. Further, these data show that enzyme incorporation may be dependent upon the number of vinyl double bonds in the modified enzyme, with maximal incorporation occurring at about 5–6 introduced double bonds per molecule.

EXAMPLE 7

Polymerization of Modified Enzyme with NVCL

The LCST for aqueous poly-NVCL solutions depends on the molecular weight of the polymer and varies from 31° C. for NVCL polymers with a molecular weight of 1,250,000 to 40° C. for NVCL polymers with a molecular weight of 15,500 [Galaev, I. Yu. & Mattiasson, B., *Enzyme Microb. Technol.* 15:354 (1993)]. However, the polymerization of NVCL in water is not straightforward because of the thermoreversibility of the polymer. NVCL monomers have a melting point of 34° C. and are virtually insoluble in pure water, whereas the NVCL polymers are readily soluble in cold water, but insoluble in water above the LCST. The obvious compromise for the polymerization is to conduct the reaction at a temperature above the melting point of NVCL. To prepare an aqueous poly-NVCL solution in this way, an oil-in-water emulsion was stirred with water for a period of several hours to days until the initial viscous or glassy emulsion turned into a homogeneous solution free of gel particles of monomer. This process occurs better and faster in the presence of different water-soluble protective colloids [Kroger, J., Schneider, R., Schupp, E. & Kerber, M., U.S. Pat. No. 5,739,195 (1998)]. However, this approach is less preferred for the preparation of reversibly soluble, catalytically active biocatalysts because prolonged stirring of warm enzyme solutions will inevitably denature the enzyme, especially in the presence of surfactants. Accordingly, NVCL was polymerized in the presence of DMSO at temperatures below 0° C. Using this approach, poly-NVCL-chymotrypsin enzyme-polymer conjugates were prepared at the concentrations shown in Example 6 for the polymerization of enzyme modified with NIPAAM.

Specifically, NVCL was dissolved in DMSO to give a 5% final concentration of monomer and a 10% (v/v) final concentration of DMSO in 10 mM phosphate buffer, pH 7.0–7.5. TEMED (40 µl) was added to each 10 ml of solution. The solution was cooled to about 0° C. The reaction was initiated by the addition of a 10% water-chilled solution of $(NH_4)_2S_2O_8$ (40 mg). The mixture was placed into a freezer at −20° C. for 18–20 hours. After thawing, turbid samples were discarded, the transparent samples were dialyzed using dialysis tubing with a molecular weight cut-off limit of 30 kDa and lyophilized, if necessary.

EXAMPLE 8

Enzyme Activity of NIPAAM-based Enzyme-polymer Conjugates

Figure 7:
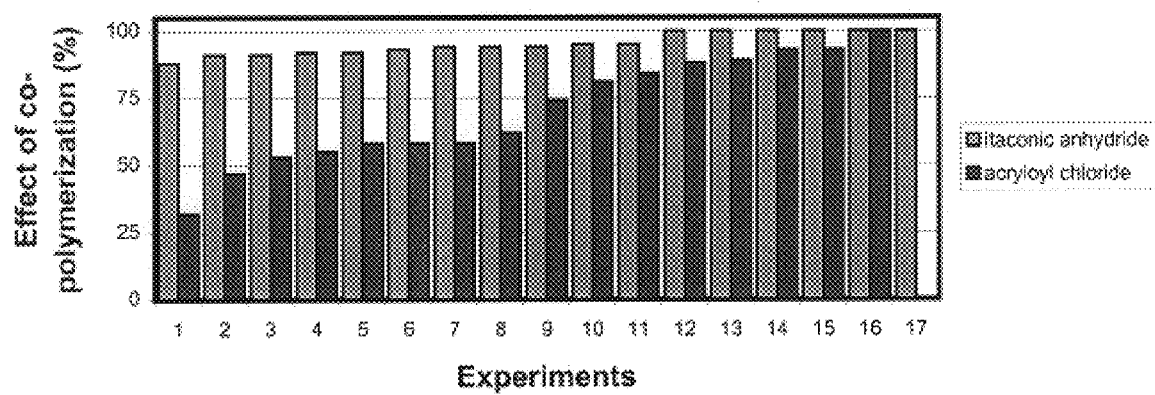
FIG. 7 depicts the percent enzyme activity retained by the enzyme-polymer conjugate products of copolymerization of NIPAAM monomers and chymotrypsin modified with either itaconic anhydride (light hatching) or acryloyl chloride (dark hatching), where 100% activity is calculated from the protein content corrected for any loss of activity during the modification step, and all data were sorted in ascending order prior to plotting.

The specific activity of the enzyme-polymer conjugates produced by the present method an important parameter. FIG. 7 shows the effect of copolymerization on enzyme activity for NIPAAM-chymotrypsin enzyme-polymer conjugates. These data were derived from activity and protein measurements and corrected for any activity loss that occurred during enzyme modification. The theoretical activity of the enzyme after incorporation into the conjugate was calculated by multiplying the protein content (experimental value) by the specific activity of the native (free) enzyme. In other words, it was assumed that the incorporation of the enzyme into the polymer either "killed" the enzyme or did not change its activity. Plotting the results of these experiments dependent upon various parameters did not reveal any regularity. Thus, the data were sorted in ascending order before plotting.

Copolymerization of chymotrypsin modified with itaconic anhydride caused very little (if any) activity loss. Average residual activity was 95% and standard deviation was 4%. Practically speaking, this result means that there was no change in activity. The effect of copolymerization on the activity of chymotrypsin modified with acryloyl chloride was more pronounced. Average residual activity was 70% and standard deviation was 20%. This is most probably the result of the heterogeneous nature of enzyme samples after modification, e.g., modification with acryloyl chloride gives a much wider distribution and this wide distribution results in a wide activity distribution after copolymerization.

Figure 8A:
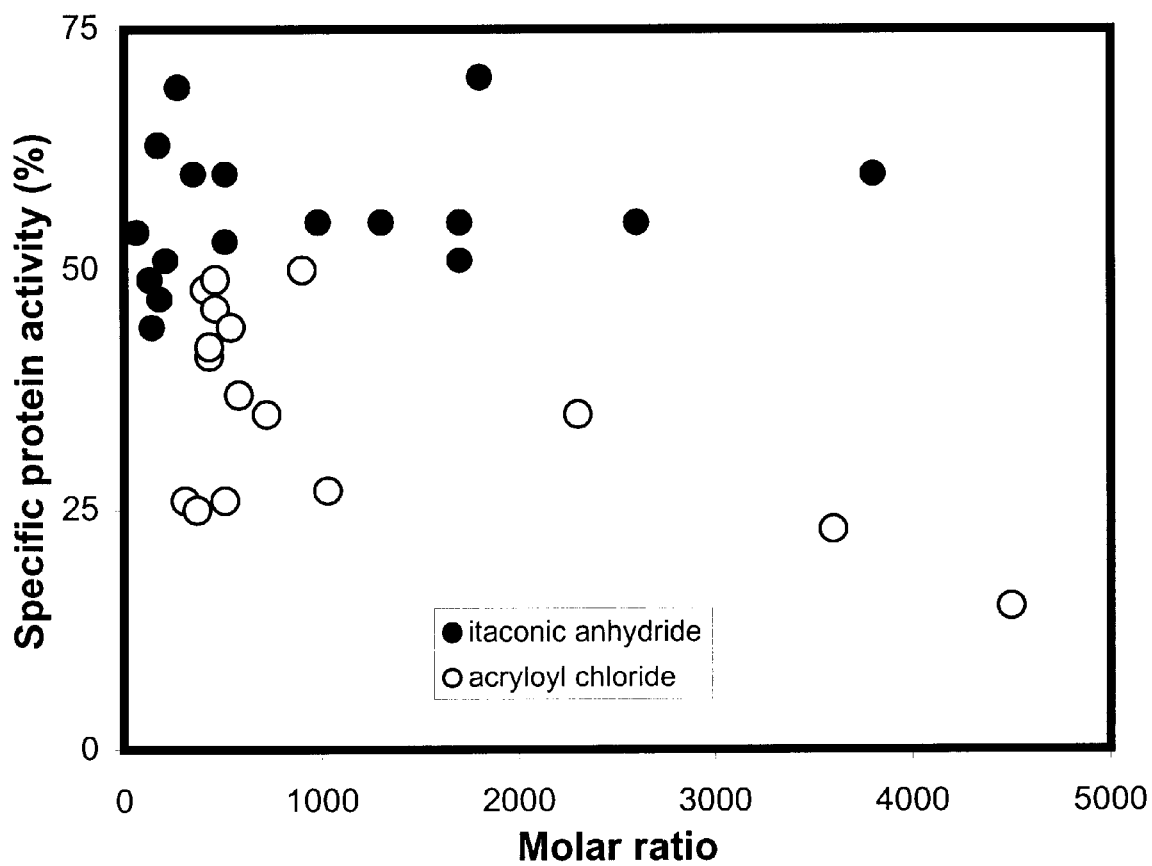
FIG. 8A depicts the percent specific activity of reversibly soluble enzyme-polymer conjugate products where percent specific protein activity equals the weight ratio of active enzyme to total protein and molar ratio equals ([NIPAAM]/([E]×(the number of double bonds))

Specific activity can be calculated in two ways. The first way is to relate active protein to total protein (specific protein activity). As shown in FIG. 8A, the specific protein activity of enzyme-polymer conjugates did not depend on the molar ratio of monomer to enzyme for either modifying agents. For enzyme-polymer conjugates prepared using chymotrypsin modified with itaconic anhydride, the specific protein activity was between 50% and 75%, with an average of 56% and standard deviation of 7%. The specific protein activity of enzyme-polymer conjugates prepared using chymotrypsin modified with acryloyl chloride was between 25% and 50%, with an average of 35% and standard deviation of 11%. In other words, the use of chymotrypsin modified with acryloyl chloride produced enzyme-polymer conjugates with a lower specific protein activity and lower reproducibility compared to enzyme-polymer conjugates produced using chymotrypsin modified with itaconic anhydride. As shown herein, the enzyme modification step was the main source of activity loss.

Figure 8B:
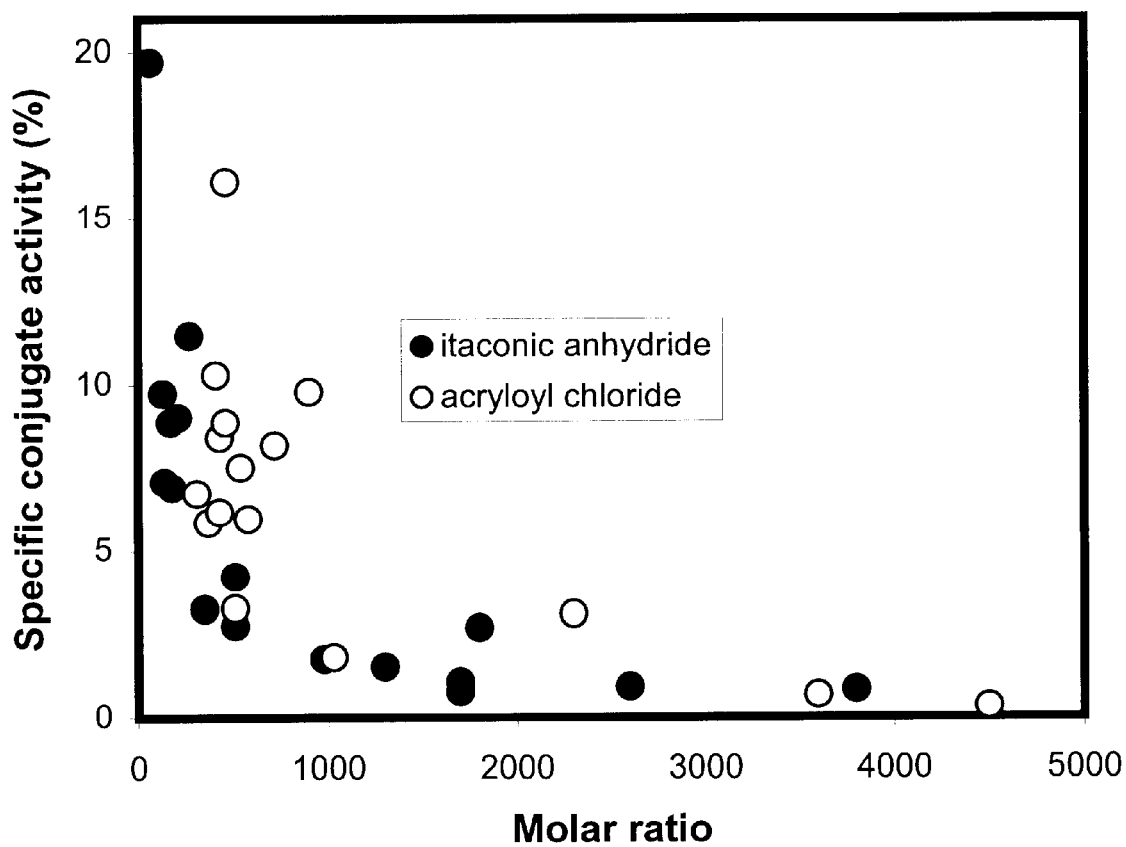
FIG. 8B depicts the percent specific conjugate activity of reversibly soluble polymer enzyme biocatalyst products where the percent specific conjugate activity equals the weight ratio of active enzyme to the total weight of the enzyme-polymer conjugate and molar ratio equals ([NIPAAM]/([E]×(the number of double bonds)).
Figure 9A:
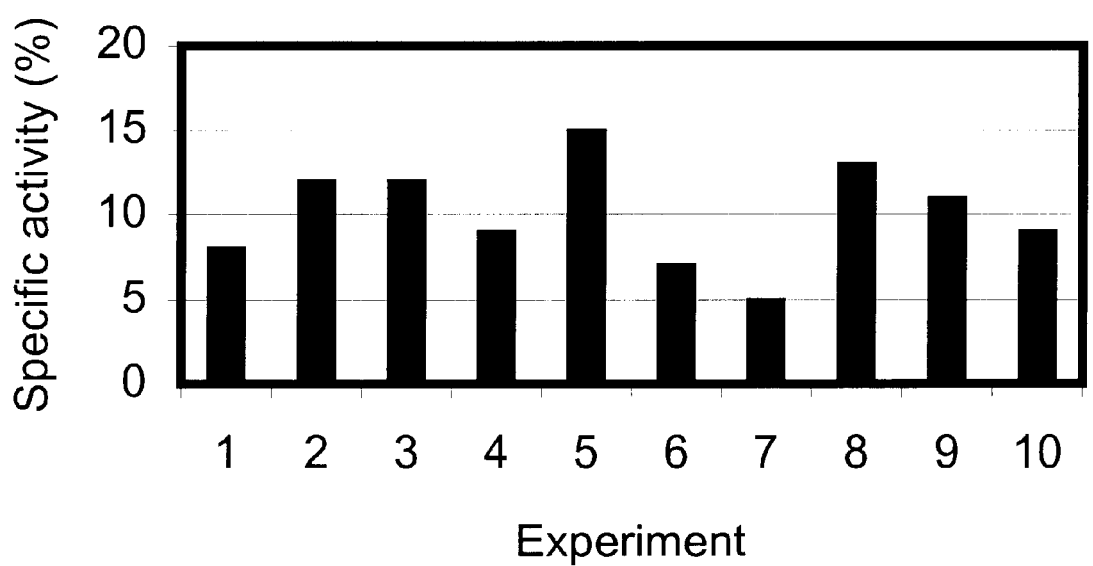
FIG. 9 depicts the percent enzyme activity retained by the enzyme-polymer conjugate products of copolymerization of NIPAAM and subtilisin Carlsberg (FIG. 9A) or NIPAAM and PS lipase (FIG. 9B), where 100% activity is the activity of equal weight amounts of respective enzymes.
Figure 9B:
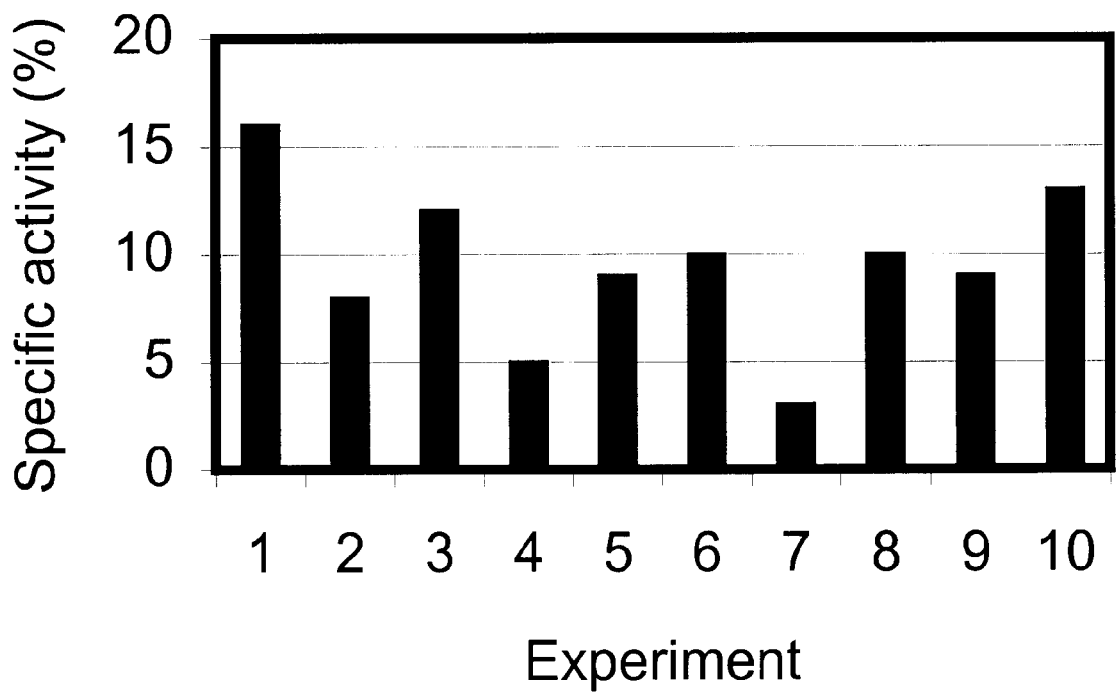

However, for practical applications it is also important to look at the specific activity of the enzyme-polymer conjugate as a whole by relating the weight of the active protein to the total weight of the conjugate biocatalyst (specific conjugate activity). The specific conjugate activity of many of the samples prepared using chymotrypsin was on the order of 10% for chymotrypsin modified with both modification reagents (FIG. 8B). The specific conjugate activity of some of the samples was close to 20%. For modification with itaconic anhydride, the average specific conjugate activity of the samples synthesized at molar ratios between 60 and 300 was 10% with standard deviation of 4%. Specific conjugate activity decreased with increased molar ratio. A higher molar ratio means a higher monomer concentration and, therefore, a higher contribution of the polymer into the total weight of the product. Specific conjugate activity of reversibly soluble, catalytically active enzyme polymer conjugates prepared using subtilisin Carlsberg and PS lipase (10 samples for each enzyme) is shown in FIG. 9. The specific conjugate activity of the biocatalysts prepared using modified subtilisin Carlsberg was 10% with a standard deviation of 3. Similarly, data for reversibly soluble, catalytically active enzyme-polymer conjugates prepared using modified PS lipase were 9.5% and with a standard deviation of 4%. These data show that, for an arbitrary enzyme, a specific conjugate activity of at least about 10% to 25% is feasible. A 10% level of specific conjugate activity is a huge increase compared to the corresponding specific conjugate activity of <1% shown for most insoluble immobilized enzymes from data discussed in the literature. The specific conjugate activities for published enzyme-polymer conjugates are as follows: chymotrypsin, 2% [Chen, J.-P. & Hsu, M.-S., *J. Mol. Catalysis B: Enzymatic,* 2:233 (1997)]; amylase, 4% [Shiroya, T., Yasui, M., Fujimoto, K & Kawaguchi, H., *Colloid Surfaces B: Biointerfaces* 4:275 (1995)]; glucosidase, 4.5% [Chen, G. & Hoffman, A. S., *J. Biomater. Sci. Polymn. Edn.* 5:371 (1994)], thermolysin, 1.2% [Liu, F., Tao, G. & Zhuo, R., *Polym. J.,* 25:561 (1993)]. The only comparable published results were obtained with a biocatalyst prepared using chymotrypsin and a polymerized liposome [Suh, Y., Jin, X.-H., Dong, X.-Y., Yu, K. & Zhou, X. Z., *Appl. Biochem. Biotechnol.,* 56:331 (1996)]. However, liposome technology is not scaleable for industrial applications and, therefore, impractical.

The higher specific conjugate activity of the reversibly soluble, catalytically active enzyme-polymer conjugate products of the present invention when compared with prior art enzymepolymer conjugates, is a direct consquence of the higher degree of incorporation of modified enzyme into the final product. Unlike prior art methods for producing reversibly soluble biocatalysts, in which enzyme is copolymerized with modified "pre-polymerized" polymer, the present method for producing reversibly soluble enzyme biocatalysts comprises copolymerizing modified enzyme with monomers and nascent polymers, i.e., polymer chain growth and protein binding occur simultaneously. For this reason, the present method results in a higher degree of incorporation of modified enzyme into the final product than prior art methods and, consequently, higher specific conjugate activity for the products of the present method. As shown in FIG. 6, the present method for producing enzyme-polymer conjugates typically has binding efficiencies above 75% when enzymes modified with itaconic anhydride are used, and at 50% or higher when enzymes modified with acryloyl chloride are used. Under the preferred conditions described herein, binding efficiencies approach 100%. Accordingly, the present method for producing enzyme-polymer conjugates is exceedingly more efficient, therefore, more cost-effective than published methods.

EXAMPLE 9
Enzyme Activity of NVCL-based Enzyme-polymer Conjugates

Figure 10:
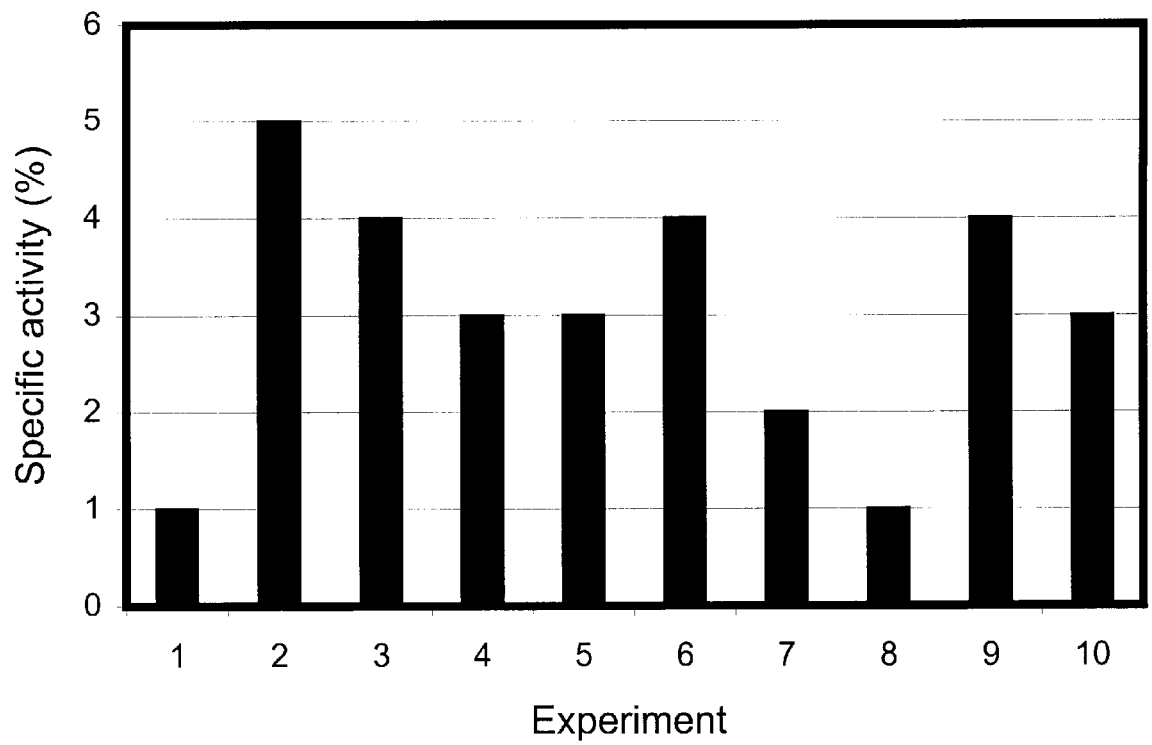
FIG. 10 depicts the percent specific conjugate activity of the enzyme-polymer conjugate products of copolymerization of NVCL and chymotrypsin modified with itaconic anhydride, where the percent specific conjugate activity equals the ratio of active enzyme by weight to the total weight of the enzyme-polymer conjugate.

Specific conjugate activity for poly-NVCL-chymotrypsin enzyme-polymer conjugates was determined as described for NIPAAM-based enzyme-polymer conjugates. As shown in FIG. 10, the specific conjugate activity of poly-NVCL-chymotrypsin polymeric enzymes was lower than the specific conjugate activity of NIPAAM-based enzyme-polymer conjugates. Nonetheless, these data indicate that the present method can be used successfully to produce reversibly soluble, catalytically active. enzyme-polymer conjugates with a variety of monomers.

EXAMPLE 10
Reuse of Reversibly Soluble Biocatalyst

The reusability of enzyme-polymer conjugates prepared using itaconic anhydride as a modifying agent was tested. The reuse of reversibly soluble, catalytically active chymotrypsin-NIPAAM conjugates was tested by measuring the isolated yield of chymotrypsin-catalyzed acyl-group transfer between AcPheOEt and LeuNH$_2$ (AcPheOEt+ LeuNH$_2$→AcPheLeuNH$_2$+EtOH) [Morihara, K. & Oka, T., *Biochem. J.*, 163:531 (1997)]. The assay product possesses low solubility in the reaction solution (9.2 mM). Solubility of AcPheOEt (50 mM) is also lower than the amount introduced into the reaction solution (100 mM). Therefore, this reaction is a good model for processes in which suspension of the starting material turns into a suspension of the product.

Specifically, a suspension of AcPheOEt (100 mM), LeuNH$_2$ (100 mM) and chymotrypsin in 0.2 M carbonate buffer (pH 10.0) containing 10% (v/v) DMF was incubated with vigorous stirring at room temperature for 2–3 minutes. The enzyme concentration was 0.5 mg/ml (0.02 mM) for free enzyme and 5 mg/ml for enzyme-polymer conjugates in a final volume of 10 ml. The initial specific conjugate activity of the biocatalyst used in these experiments was 11%. Following incubation, the precipitate was filtered. The precipitate was washed with water (1–2 ml), air-dried and weighed. During the enzyme assay, the pH of the filtrate was maintained between 6.5–7.5 with 2 M HCl to minimize exposure of the enzyme to high pH. The enzyme-polymer conjugate was precipitated with 5 M NaCl (10 ml), filtered and introduced into the next reaction cycle without drying.

Figure 11:
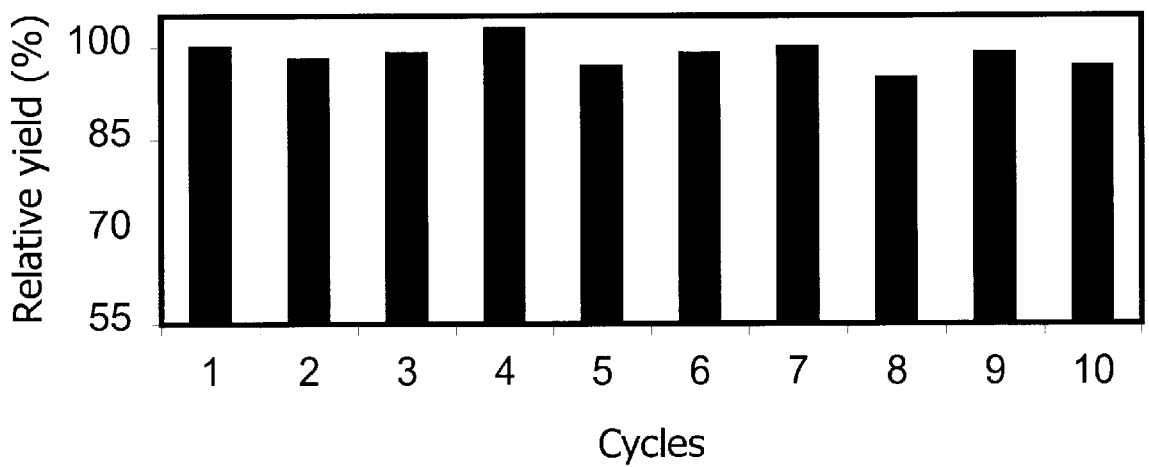
FIG. 11 depicts the cycle-to-cycle change in product yield of chymotrypsin-NIPAAM enzyme-polymer conjugates through ten cycles.

Product yield is an expression of the experimental weight of a product divided by the theoretical weight (100%) of the product, and is the most important parameter when determining the efficiency of enzyme-polymer conjugate reuse. Control assays were performed with free enzyme as described in the literature [Morihara, K. & Oka, T., *Biochem. J.*, 163:531 1997)] and gave a product yield of 84%; slightly higher than reported in the literature (80%). The results of these experiments are shown in FIG. 11. The isolated yield changed very little in these experiments. These data demonstrate that the methods of the present invention can be used to make reversibly soluble, catalytically active enzyme-polymer conjugates which not only have greater activities than conjugates produced by published methods, but which also can be reused with at least as much success or more than published methods and products.

What is claimed is:

1. A reversibly soluble, catalytically active enzyme-polymer conjugate made by a process comprising:
   (a) contacting a free enzyme having at least one free amino group with a modifying agent, the modifying agent having at least one vinyl double bond and an active acylating group, the active group forming an amide bond between the modifying agent and the free amino group of the enzyme and producing a modified enzyme having a free vinyl double bond;
   (b) recovering the modified enzyme;
   (c) contacting the modified enzyme with a soluble monomer having the structure $R_1R_2CCR_3R_4$, wherein $R_1$ is selected from hydrogen, carboxy or phenyl moieties, $R_2$ is a hydrogen moiety; $R_3$ is selected from hydrogen, methyl, carboxy, sulfo, or 2-pyridine moieties and $R_4$ is selected from hydrogen, methyl, methoxy, aminopropyl, N,N-dimethylaminopropyl, N,N-diethylaminopropyl,

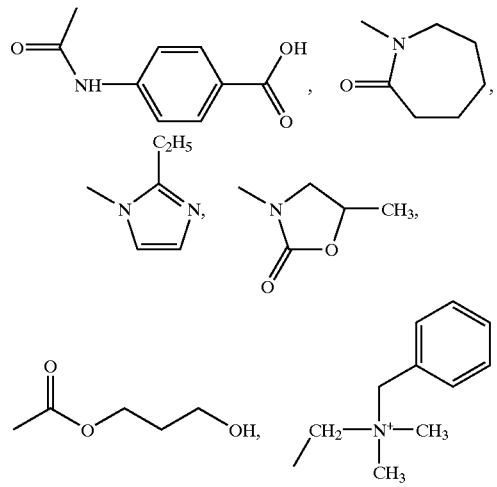

or $C(O)NR_5R_6$, wherein $R_5$ is selected from hydrogen, methyl, ethyl, propyl, iso-propyl, or propyl, tetrahydropyran-2-yl, 2-methoxy-ethyl, $R_6$ is selected from ethyl, propyl, iso-propyl, cyclo-propyl, tetrahydropyrano-2-yl, 2-methoxy-ethyl, 3-methoxy-propyl, 3-iso-propoxy-propyl or —C(CH$_3$)$_2$—C(O)—NHR$_7$, wherein R$_7$ is selected from methyl, ethyl, iso-propyl, 3-methoxy-propyl or 2,2-diethoxy-ethyl, and wherein the monomer is dissolved in a solution and is selected from a group of monomers which when polymerized contain both hydrophobic and hydrophilic regions; and
   (d) contacting an initiating agent or agents with the monomer, thereby causing a bond to form between the modified enzyme and the monomer and producing an active enzyme-polymer conjugate that reversibly changes its solubility upon a change in the temperature, salt concentration or pH of the solution.

2. The product of claim 1 wherein the free enzyme is chymotrypsin.

3. The product of claim 1 where the free enzyme is subtilisin.

4. The product of claim 1 wherein the free enzyme is PS lipase.

5. The product of claim 1 wherein the modifying agent is itaconic anhydride.

6. The product of claim 5 wherein the ratio of itaconic anhydride to free enzyme is in the range of about 0.2 mg to about 2 mg of itaconic anhydride per mg of free enzyme.

7. The product of claim 5 wherein the ratio of itaconic anhydride to free enzyme is in the range of about 1 mg to about 1.5 mg of itaconic anhydride per mg of free enzyme.

8. The product of claim 1 wherein the modifying agent is acryloyl chloride.

9. The product of claim 8 wherein the ratio of acryloyl chloride to free enzyme is in the range of about 0.5 ml to about 2.5 ml of acryloyl chloride per gram of free enzyme.

10. The product of claim 8 wherein the ratio of acryloyl chloride to free enzyme is about 1.5 ml of acryloyl chloride per gram of free enzyme.

11. The product of claim 1 wherein the monomer is N-iso-propylacrylamide.

12. The product of claim 1 wherein the monomer is N-vinylcaprolactam.

13. The product of claim 1 wherein the solution in step (d) is an aqueous solution.

14. The product of claim 13 wherein the solution is a 50–100 mM phosphate buffer solution.

15. The product of claim 14 wherein the solution further comprises 10% (v/v) dimethyl sulfoxide.

16. The product of claim 1 wherein the initiating agents are $(NH_4)_2S_2O_8$ and N,N,N',N',-tetramethylethylenediamine.

17. The product of claim 1 wherein the initiating agents are $Na_2S_2O_6$ and N,N,N',N',-tetramethylethylenediamine.

18. The product of claim 1 wherein the initiating agents are 2,2'-azobis(2-aminopropane)dihydrochloride and 2,2'-azobis[2-(2-imidazoline-2-yl)propane]dihydrochloride.

* * * * *

UNITED STATES PATENT AND TRADEMARK OFFICE
CERTIFICATE OF CORRECTION

PATENT NO.   : 6,433,078 B1
DATED        : August 13, 2002
INVENTOR(S)  : Mikhail Y. Gololobov and Victor M. Ilyashenko It is certified that error appears in the above-identified patent and that said Letters Patent is hereby corrected as shown below:

<u>Title page,</u>
Item [73], please delete "Shrewsbury, MA" and substitute therefore
-- Hoffman Estates, IL --.

Signed and Sealed this

Third Day of December, 2002

JAMES E. ROGAN
*Director of the United States Patent and Trademark Office*